United States Patent
Han et al.

(10) Patent No.: US 7,435,320 B2
(45) Date of Patent: Oct. 14, 2008

(54) METHODS AND APPARATUSES FOR MONITORING ORGANIC ADDITIVES IN ELECTROCHEMICAL DEPOSITION SOLUTIONS

(75) Inventors: Jianwen Han, Danbury, CT (US); Mackenzie E. King, Southbury, CT (US); Weihua Wang, Danbury, CT (US); Glenn Tom, New Milford, CT (US); Jay Jung, Sunnyvale, CA (US)

(73) Assignee: Advanced Technology Materials, Inc., Danbury, CT (US)

( * ) Notice: Subject to any disclaimer, the term of this patent is extended or adjusted under 35 U.S.C. 154(b) by 439 days.

(21) Appl. No.: 10/836,546

(22) Filed: Apr. 30, 2004

(65) Prior Publication Data

US 2005/0241948 A1  Nov. 3, 2005

(51) Int. Cl.
*G01N 27/403* (2006.01)
(52) U.S. Cl. .................................. 204/409; 204/434
(58) Field of Classification Search ................. 204/409, 204/412, 434, 400, 411
See application file for complete search history.

(56) References Cited

U.S. PATENT DOCUMENTS

| | | | |
|---|---|---|---|
| 2,707,166 A | 4/1955 | Brown et al. | |
| 2,707,167 A | 4/1955 | Hoover et al. | |
| 2,830,014 A | 4/1958 | Gundel et al. | |
| 2,884,366 A * | 4/1959 | Anderson et al. | 204/408 |
| 2,898,282 A | 8/1959 | Flook, Jr. et al. | |
| 3,101,305 A | 8/1963 | Roth et al. | |
| 3,276,979 A | 10/1966 | Strauss et al. | |
| 3,288,690 A | 11/1966 | Creutz et al. | |
| 3,498,888 A * | 3/1970 | Johansson | 205/793 |
| 3,655,534 A | 4/1972 | Kampe | |
| 3,725,220 A | 4/1973 | Kessler | |
| 3,798,138 A | 3/1974 | Ostrow et al. | |
| 3,883,414 A | 5/1975 | Fujinaga et al. | |

(Continued)

FOREIGN PATENT DOCUMENTS

| | | |
|---|---|---|
| DE | 19911447 A1 | 12/2000 |
| EP | 0 302 009 A1 | 7/1988 |
| JP | 2001-073183 A | 3/2001 |
| WO | WO 01/25774 A1 * | 4/2001 |
| WO | WO-01/29548 A1 | 4/2001 |

OTHER PUBLICATIONS

Aleander Milcheve and Irene Montenegro, J. Electroanal. Chem., 333 (1992), pp. 93-102.

(Continued)

*Primary Examiner*—Kaj K Olsen
(74) *Attorney, Agent, or Firm*—Steven J. Hultquist; Intellectual Property/Technology Law; Maggie Chappuis

(57) ABSTRACT

The present invention relates in general to real-time analysis of electrochemical deposition (ECD) metal plating solutions, for the purpose of reducing plating defects and achieving high quality metal deposition. The present invention provides various new electrochemical analytical cell designs for reducing cross-contamination and increasing analytical signal strength. The present invention also provides improved plating protocols for increasing potential signal strength and reducing the time required for each measurement cycle. Further, the present invention provides new methods and algorithms for simultaneously determining concentrations of suppressor, accelerator, and leveler in a sample ECD solution within three experimental runs. A particularly preferred embodiment of the present invention provides a method for simultaneously determining concentrations of all three organic additives within a single experimental run by using a single analytical cell, while interactions between such additives are properly accounted for.

13 Claims, 6 Drawing Sheets

U.S. PATENT DOCUMENTS

| | | | | |
|---|---|---|---|---|
| 3,910,830 | A | * | 10/1975 | Mayse .................. 204/404 |
| 3,950,234 | A | | 4/1976 | Faulkner et al. |
| 3,972,789 | A | | 8/1976 | Eppensteiner et al. |
| 3,996,124 | A | * | 12/1976 | Eaton et al. ............ 204/404 |
| 4,038,161 | A | | 7/1977 | Eckles et al. |
| 4,071,429 | A | * | 1/1978 | Wagenknecht et al. ... 204/229.1 |
| 4,119,532 | A | * | 10/1978 | Park ..................... 209/17 |
| 4,132,605 | A | | 1/1979 | Tench et al. |
| 4,260,950 | A | * | 4/1981 | Hadden et al. .......... 324/438 |
| 4,305,039 | A | | 12/1981 | Steuernagel et al. |
| 4,317,002 | A | | 2/1982 | Spicer |
| 4,388,165 | A | | 6/1983 | Koshiishi et al. |
| 4,496,454 | A | * | 1/1985 | Berger .................. 204/402 |
| 4,498,039 | A | | 2/1985 | Galwey et al. |
| 4,529,495 | A | | 7/1985 | Marsoner |
| 4,568,445 | A | | 2/1986 | Cates et al. |
| 4,570,492 | A | * | 2/1986 | Walsh ................. 73/861.05 |
| 4,589,958 | A | | 5/1986 | Alexander et al. |
| 4,595,462 | A | | 6/1986 | Vangaever et al. |
| 4,707,378 | A | | 11/1987 | McBride et al. |
| 4,772,375 | A | | 9/1988 | Wullschleger et al. |
| 4,812,210 | A | | 3/1989 | Bonivert et al. |
| 4,849,330 | A | | 7/1989 | Humphries et al. |
| 4,917,774 | A | | 4/1990 | Fisher |
| 4,917,777 | A | | 4/1990 | Fisher |
| 5,017,860 | A | | 5/1991 | Germer et al. |
| 5,074,157 | A | | 12/1991 | Marsoner et al. |
| 5,131,999 | A | * | 7/1992 | Gunasingham ........ 204/403.02 |
| 5,162,077 | A | | 11/1992 | Bryan et al. |
| 5,192,403 | A | | 3/1993 | Chang et al. |
| 5,223,118 | A | | 6/1993 | Sonnenberg et al. |
| 5,268,087 | A | | 12/1993 | Lu |
| 5,288,387 | A | | 2/1994 | Ito et al. |
| 5,296,123 | A | * | 3/1994 | Reddy et al. ............ 205/775 |
| 5,316,649 | A | | 5/1994 | Kronberg |
| 5,320,721 | A | | 6/1994 | Ludwig et al. |
| 5,325,038 | A | | 6/1994 | Banzai et al. |
| 5,352,350 | A | | 10/1994 | Andricacos et al. |
| 5,404,018 | A | | 4/1995 | Yasuda et al. |
| 5,447,802 | A | | 9/1995 | Tobiyama et al. |
| 5,462,645 | A | * | 10/1995 | Albery et al. ............ 205/778 |
| 5,612,698 | A | | 3/1997 | Reay |
| 5,635,043 | A | | 6/1997 | Tur'yan et al. |
| 6,022,470 | A | * | 2/2000 | Yarnitzky ................ 205/775 |
| 6,210,640 | B1 | | 4/2001 | Ruth et al. |
| 6,231,743 | B1 | | 5/2001 | Etherington |
| 6,254,760 | B1 | | 7/2001 | Shen et al. |
| 6,270,651 | B1 | | 8/2001 | Essalik et al. |
| 6,280,602 | B1 | | 8/2001 | Robertson |
| 6,288,783 | B1 | | 9/2001 | Auad |
| 6,365,033 | B1 | | 4/2002 | Graham et al. |
| 6,366,794 | B1 | | 4/2002 | Moussy et al. |
| 6,395,152 | B1 | | 5/2002 | Wang |
| 6,409,903 | B1 | | 6/2002 | Chung et al. |
| 6,458,262 | B1 | | 10/2002 | Reid |
| 6,459,011 | B1 | | 10/2002 | Tarr et al. |
| 6,478,950 | B1 | | 11/2002 | Peat et al. |
| 6,495,011 | B2 | | 12/2002 | Robertson |
| 6,558,519 | B1 | | 5/2003 | Dodgson et al. |
| 6,569,307 | B2 | | 5/2003 | Blachier et al. |
| 6,572,753 | B2 | | 6/2003 | Chalyt et al. |
| 6,592,737 | B1 | | 7/2003 | Robertson |
| 6,645,364 | B2 | | 11/2003 | Calvert et al. |
| 6,673,226 | B1 | | 1/2004 | Kogan et al. |
| 6,709,568 | B2 | | 3/2004 | Han et al. |
| 6,758,955 | B2 | | 7/2004 | Robertson |
| 6,758,960 | B1 | | 7/2004 | Robertson |
| 6,808,611 | B2 | | 10/2004 | Sun et al. |
| 6,827,839 | B2 | | 12/2004 | Sonnenberg et al. |
| 6,974,531 | B2 | | 12/2005 | Andricacos et al. |
| 6,984,299 | B2 | | 1/2006 | Han et al. |
| 7,022,215 | B2 | | 4/2006 | Schomburg |
| 7,094,323 | B2 | | 8/2006 | King et al. |
| 2002/0070708 | A1 | | 6/2002 | Wu |
| 2003/0080000 | A1 | | 5/2003 | Robertson |
| 2004/0040842 | A1 | | 3/2004 | King et al. |
| 2004/0055888 | A1 | | 3/2004 | Wikiel et al. |
| 2004/0065561 | A1 | | 4/2004 | Chalyt et al. |
| 2005/0016847 | A1 | | 1/2005 | Buehler |
| 2005/0067304 | A1 | | 3/2005 | King et al. |
| 2005/0109624 | A1 | | 5/2005 | King et al. |
| 2005/0224370 | A1 | | 10/2005 | Liu et al. |
| 2005/0241948 | A1 | | 11/2005 | Han et al. |
| 2005/0247576 | A1 | | 11/2005 | Tom et al. |
| 2006/0102675 | A1 | | 5/2006 | Han et al. |
| 2006/0266648 | A1 | | 11/2006 | King et al. |

OTHER PUBLICATIONS

Alwash, S. H. et al., A rotating disc electrode with heat transfer facilities for corrosion studies, Corrosion Science, 1987, pp. 383-390, vol. 27, No. 4.

Bard, Allen J., et al., Electrochemical Methods: Fundamentals and Applications, 2nd Edition, 2001, pp. 15-16, Publisher: John Wiley & Sons, Inc., Published in: New York.

Barz, H., et al., Measurement of the surface temperature of rotating electrodes, J. Electroanal. Chem., 1976, pp. 415-418, vol. 69.

Cerna, N., Determination of chlorides in an acid copper-plating bath, Povrchove Upravy, 1973, pp. 11-12, vol. 13, No. 6.

Cheng, X. L., et al., Analysis of organic additives in copper-plating brightener by high performance liquid chromatography, Se. Pu., Nov. 1999, pp. 602-603, vol. 17, No. 6.

Dikusar, A. I., et al., Thermokinetic instability of electrode processes, J. Electroanal. Chem., 1986, pp. 11-23, vol. 207.

Freeman, J.E., et al., A fiber-optic absorption cell for remote determination of copper in industrial electroplating baths, Analytica Chimica Acta, 1985, pp. 121-128, vol. 177.

Freitag, Walter O., et al., Determination of the individual additive components in acid copper plating baths, Plat. Surf. Fin., Oct. 1983, pp. 55-60, vol. 70, No. 10.

Healy, John P., et al., The chemistry of the additives in an acid copper electroplating bath: Part II. The instability 4,5-dithiaoctane-1, . . . , J. Electoanal. Chem., Oct. 1992, pp. 167-177, vol. 338, No. 1-2.

Healy, John P., et al., The chemistry of the additives in an acid copper electroplating bath: Part III. The mechanism of brightening by 4,5- . . . , J. Electroanal. Chem., Oct. 1992, pp. 179-187, vol. 338, No. 1-2.

Huiliang, Huang, et al., Flow potentiometric and constant-current stripping analysis for mercury(II) with gold, platinum and carbon fibre . . . , Analytica Chimica Acta, 1987, pp. 1-9, vol. 201.

Kim, Jae Jeong, et al., Catalytic behavior of 3-mercapto-1-propane sulfonic acid on Cu electrodeposition and its effect on Cu film properties . . . , J. Electronanal. Chem., Jan. 30, 2003, pp. 61-66, vol. 542, No. 1.

Kruglikov, S. S., et al., The effect of some primary and secondary brighteners on the double layer capacitance in nickel electrodeposition, Electrochimica Acta, Sep. 1967, pp. 1263-1271, vol. 12, No. 9.

Liu, Yonghui, Testing Technology of Electrochemistry, (English relevance attached), 1987, pp. 159, Published in: Beijing.

Merriam-Webster's Collegiate Dictionary: 10th Ed., 1998, pp. 328, 361, 478.

Metrohm, Product description of 731 Relay Box, Downloaded May 11, 2005 from http://www.metrohm.com/products/05/acc/731/731.html, May 11, 2005.

Metrohm, Product description of 772 Pump Unit, Downloaded May 11, 2005 from http://www.metrohm.com/products/05/acc/772/772.html, May 11, 2005.

Metrohm, Product description of MVA-3 voltammetry system, Downloaded May 11, 2005 from http://www.metrohm.com/products/06/mva/mva03/mva03.html, May 6, 2004.

Metrohm, Product description of Titrando Dosino, http://www.metrohm.com/titrando/products/units/800/800.html, 2003.

Metrohm, Product description of Titrando PC Control, Downloaded May 11, 2005 from http://www.metrohm.com/titrando/products/control/pc/pc.html, 2004.

Oldham, Keith B., et al., Fundamentals of Electrochemical Science, 1994, pp. 328-332, Publisher: Academic Press, Inc., Published in: San Diego.

Seisler, H.W., et al., Near Infrared Spectroscopy, Near Infrared Spectroscopy, 2002, Publisher: Wiley.

Skoog, Douglas A., et al., Principles of Instrumental Analysis, 3rd Ed., 1985, pp. 332-337, Publisher: Harcourt College Publishers.

Tench, Dennis, et al., Cyclic pulse voltammetric stripping analysis of acid copper plating baths, J. Electrochem. Soc., Apr. 1985, pp. 831-834, vol. 132, No. 4.

Vereecken, P.M., et al., The chemistry of additives in damascene copper plating, IBM J. Res. Dev., Jan. 2005, pp. 3-18, vol. 49, No. 1.

Wojciechowski, Marek, et al., Square-wave anodic stripping voltammetry of lead and cadmium at cylindrical graphite fiber microelectrodes with . . . , Analytica Chimica Acta, 1991, pp. 433-445, vol. 249, No. 2.

Wikipedia, Universal Serial Bus—Wikipedia, Downloaded May 11, 2005 from hhtp://en.wikipedia.org/wiki/USB, May 11, 2005.

Wyche, et al., Constant low-voltage drop rotating electrode assembly, Electrochemical Technology, 1966, pp. 447, vol. 4, No. 7-8.

"Aldrich Handbook of Fine Chemicals and Laboratory Equipment", 2003-2004, pp. 500, 501 and 1634, Publisher: Aldrich Chemical Co., Published in: Milwaukee, WI.

* cited by examiner

METHODS AND APPARATUSES FOR MONITORING ORGANIC ADDITIVES IN ELECTROCHEMICAL DEPOSITION SOLUTIONS

BACKGROUND OF THE INVENTION

1. Field of the Invention

This invention relates generally to methods and apparatuses for conducting organic analysis of electrochemical deposition solutions, especially for monitoring organic additive concentrations in electrochemical copper plating baths.

2. Background of the Invention

In the practice of copper interconnect technology in semiconductor manufacturing, electrochemical deposition (ECD) is widely employed for forming copper interconnect structures on microelectronic substrates. The Damascene process, for example, uses physical vapor deposition to deposit a seed layer of copper on a barrier layer, followed by electrochemical deposition of copper.

In the ECD operation, organic additives as well as inorganic additives are employed in the plating solution in which the metal deposition is carried out. The ECD process is sensitive to concentration changes of both the organic and inorganic components. Since concentrations of these components can vary considerably as they are consumed during the life of the bath, it therefore is necessary to conduct real-time monitoring and replenishment of all major bath components to ensure optimal process efficiency and yield of the semiconductor product incorporating the electrodeposited copper.

Inorganic components of the copper ECD bath include copper, sulfuric acid and chloride, which may be measured by potentiometric analysis. Organic additives such as suppressors, accelerators, and levelers are added to the ECD bath to control uniformity of the film thickness across the wafer surface. The concentration of the organic additives can be measured by pulsed cyclic galvanostatic analysis (PCGA), which mimics the plating conditions occurring on the wafer surface. In the practice of the PCGA method, copper is electroplated onto a working or testing electrode, by supplying a sufficient current (or potential), while monitoring the corresponding potential (or current). The electrical potential (or current) measured during such electroplating step correlates with the organic additive concentrations in the sample electroplating bath, and therefore can be used for determining concentrations of organic additives. For further details regarding the PCGA processes, please see U.S. Pat. No. 6,280,602 issued Aug. 28, 2001 to Peter M. Robertson for "Method and Apparatus for Determination of Additives in Metal Plating Baths," the disclosure of which hereby is incorporated herein by reference for all purposes.

There is a continuing need to improve the PCGA analysis of organic additives in ECD baths and to provide more stable analytical signals and to reduce noise and measurement errors.

There is a further need to modify the conventional PCGA procedures to achieve shorter calibration and measurement cycles, reduce the analysis time, and simplify the hardware and software required for performing the PCGA analysis.

There is still a further need to account for interactions between the different types of organic additives and their impact on the PCGA analysis results.

Other objects and advantages will be more fully apparent from the ensuring disclosure and appended claims.

SUMMARY OF THE INVENTION

The present invention relates generally to real-time analysis of ECD metal plating solutions, for the purpose of reducing plating defects and achieving high quality metal deposition.

In one aspect, the invention relates to use of a microelectrode that has a longitudinal axis and an average transverse dimension (i.e., as measured along a direction that is perpendicular to its longitudinal axis) of from about 1 $\mu$m to about 250 $\mu$m in an electrochemical analytical cell for analyzing a sample electrochemical deposition solution. Such electrochemical analytical cell specifically comprises (1) a measurement chamber for receiving the sample electrochemical deposition solution, such measurement chamber being in fluid communication with at least one liquid inlet and at least one liquid outlet, (2) a test electrode, a counter electrode, and a reference electrode positioned in the measurement chamber for contacting the sample electrochemical deposition solution, wherein the test electrode is a microelectrode as described hereinabove. Such microelectrode may comprise platinum or platinum alloy.

In another aspect, the invention relates to an electrochemical analytical cell for analyzing a sample electrochemical deposition solution, which has a flow-through configuration. Specifically, such electrochemical analytical cell comprises (1) a measurement chamber for receiving the sample electrochemical deposition solution, such measurement chamber being in fluid communication with at least one liquid inlet and at least one liquid outlet, thereby defining a liquid pathway therethrough, (2) a test electrode, a counter electrode, and a reference electrode positioned in such measurement chamber for contacting the sample electrochemical deposition solution, wherein each of the test electrode, the counter electrode, and the reference electrode comprises one or more liquid-contacting surfaces, and wherein the test electrode, the counter electrode, and the reference electrode are arranged and constructed so that all of the liquid-contacting surfaces of said electrodes are aligned with one or more surfaces of the liquid inlet, the liquid outlet, and/or the measurement chamber, and that the liquid pathway is free of blockage by the electrodes.

In order to reduce or avoid blockage of the liquid pathway, at least one or both of the test electrode and reference electrode can be embedded in a wall of the measurement chamber, while such test and/or reference electrode(s) comprises (1) electrical connectors extending outside of the measurement chamber and (2) a liquid-contacting surface aligned with an inner surface of the measurement chamber for contacting sample electrochemical deposition solution in the measurement chamber.

Further, the counter electrode can comprise a tubular element with an inner surface and an outer surface and form a part of the liquid outlet for the sample electrochemical deposition solution to pass therethrough. In such manner, such counter electrode can maintain contact with the sample electrochemical deposition solution at its inner surface, while concurrently being connected with external electrical connectors at its outer surface for measurement purposes.

A further aspect of the invention relates to an electrochemical analytical cell for analyzing a sample electrochemical deposition solution. Such electrochemical cell comprises a measurement chamber comprising an inner volume defined by a bottom surface, a top surface and a chamber wall therebetween, for receiving the sample electrochemical deposition solution. Such measurement chamber is in fluid communication with at least one liquid inlet and at least one liquid outlet. A test electrode, a counter electrode, and a reference electrode extend from the top surface of the measurement chamber downwardly into the inner volume thereof, for contacting the sample electrochemical deposition solution contained therein, while the liquid inlet comprises an opening on the bottom surface of the measurement chamber, so as to introduce liquid from the bottom surface upwardly into the inner volume of the measurement chamber.

A first and a second liquid outlet can be provided for discharging overflowed liquid from the measurement chamber. Specifically, the first liquid outlet comprises a first opening on the chamber wall for discharging a first liquid (e.g., the sample electrochemical deposition solution after measurement), and the second liquid outlet comprises a second opening on the chamber wall for discharging a second liquid (e.g., a cleaning solution) that is different from said first liquid. The distance between the first opening and the bottom surface of the measurement chamber is less than distance between the second opening and the bottom surface of the measurement chamber. In this manner, the second liquid is capable of rinsing the first opening when discharged through the second opening.

Further, at least one of the first and second liquid outlets comprises a liquid passage in fluid communication with the respective opening, wherein such liquid passage is slightly slanted so as to prevent liquid backflow into the inner volume of the measurement chamber.

The above-described new features associated with the electrochemical analytical cell can be employed either independently or jointly to construct new electrochemical cells having enhanced performance and reduced risk of sample cross-contamination.

A still further aspect of the present invention relates to a method for electrochemically depositing a metal onto an electrode surface, comprising the steps of:
  (a) providing a working electrode and a counter electrode that are both in contact with an electrochemical deposition solution comprising one or more metal ions;
  (b) applying a potential pulse between the working and counter electrodes for a sufficient period of time to induce metal nucleation on an surface of the working electrode;
  (c) subsequently, applying a constant plating current between the working and counter electrodes sufficient for effectuating electrochemical deposition of metal onto the surface of the working electrode.

Another aspect of the present invention relates to a method for electrochemically determining concentration of one or more target components in a sample electrochemical deposition solution, comprising the steps of:
  (a) contacting a working electrode and a counter electrode with the sample electrochemical deposition solution;
  (b) applying a potential pulse between the working and counter electrodes for a sufficient period of time to induce metal nucleation on an surface of the working electrode;
  (c) subsequently, applying a constant plating current between the working and counter electrodes sufficient for effectuating electrochemical deposition of metal onto the surface of the working electrode from the sample electrochemical deposition solution;
  (d) monitoring potential response of the sample electrochemical deposition solution under the constant plating current; and
  (e) determining concentration of one or more target components in such sample electrochemical deposition solution, based on the potential response of the sample electrochemical deposition solution measured under the constant plating current.

Preferably, such sample electrochemical deposition solution is a copper electroplating solution that comprises copper sulfate, sulfuric acid, chloride, and one or more organic additives such as suppressors, accelerators, and levelers, while the target components for concentration analysis are the one or more organic additives.

Yet another aspect of the present invention relates to a method for conducting electrochemical analysis of a sample electrochemical deposition solution, said method comprising the steps of providing a measurement chamber having a measuring electrode, a counter electrode, and a reference electrode therein, and performing in such measurement chamber one or more measurement cycles by using said sample electrochemical deposition solution. Each of such measurement cycles comprises the sequential steps of:
  (a) electrostripping the measuring electrode to remove metal residue formed thereon during a previous measurement cycle;
  (b) applying a cyclic electropotential between the measuring and counter electrodes to remove organic residue formed on the measuring electrode during a previous measurement cycle;
  (c) filling the measurement chamber with fresh sample electrochemical deposition solution and allowing the measuring electrode and counter electrode to reach an equilibrium state in the sample solution;
  (d) electrochemically depositing metal onto the measuring electrode by applying a constant electrical current between the measuring electrode and counter electrode through the sample electrochemical deposition solution, while concurrently monitoring potential response of the sample solution; and
  (e) applying an electropotential between the measuring electrode and counter electrode to remove at least a part of the metal deposit formed on the measuring electrode.

Preferably, the sample electrochemical deposition solution is a copper electroplating solution that comprises copper sulfate, sulfuric acid, chloride, and one or more organic additives such as suppressors, accelerators, and levelers.

An electrolytic cleaning solution comprising sulfuric acid can be used for electrostripping in step (a). More preferably, a part the electrostripping is conducted while such electrolytic cleaning solution is flushed through the measurement chamber, to remove metal residues that have been stripped of the measuring electrode and avoid further contamination of the measurement chamber by such metal residues.

Such electrolytic cleaning solution may also be used to flush the measurement chamber when the cyclic electropotential is applied between the measuring and counter electrodes (i.e., cyclic voltammetry or CV scan) in step (b), to remove organic residues that come off the electrode surface during the CV scan.

The equilibrium state in step (c) may be reached by disconnecting the measuring electrode from the counter electrode, to form an open circuit. Alternatively, such equilibrium state can be reached by applying a predetermined electropotential that is less than the copper plating potential between the measuring electrode and the counter electrode.

The electroplating in step (d) is preferably preceded by a potential pulse of from about $-0.1V$ to about $-1V$, to facilitate formation of metal nuclei on the electrode surface, and followed by a stripping electropotential of from about $0.1V$ to about $0.5V$, to remove at least a part of the metal plate formed during step (d) and thereby reduce the risk of alloying between such metal plate and metal component of the measuring electrode.

Still another aspect of the present invention relates to a method for simultaneously determining concentrations of suppressor, accelerator, and leveler in a sample electrochemical deposition solution, comprising the steps of:

(a) identifying one or more non-compositional variables that have significant impact on electropotential responses of electrochemical deposition solutions during electrochemical metal deposition;

(b) establishing a multiple regression model that expresses the electropotential responses of electrochemical deposition solutions as a function of (1) such one or more non-compositional variables, (2) organic additive concentrations in the solutions, and the corresponding coefficients;

(c) conducting multiple calibration runs, by measuring electropotential responses of multiple calibration solutions having unique, known organic additive concentrations at unique, predetermined values of said one or more variables;

(d) determining the coefficients that correspond to said one or more variables and the organic additive concentrations in the multiple regression model, based on information obtained from the calibration runs; and (e) conducting three experimental runs, by measuring electropotential responses of the sample electrochemical deposition solution at unique, predetermined values of said one or more variables;

(f) establishing three equations based on the established multiple regression model, said equations containing the coefficients determined in step (d), the electropotential responses measured during the three experimental runs in step (e) and the corresponding predetermined values of said one or more variables, and the unknown concentrations of the suppressor, accelerator, and leveler in the sample electrochemical deposition solution; and (g) calculating said suppressor, accelerator, and leveler concentrations in the sample solution by solving the three equations provided in step (f).

Preferably, analysis of variance is used for identifying the non-composition variables that have significant impact on the electropotential responses of the electrochemical deposition solutions. Specifically, a preliminary multiple regression model including terms for all non-compositional variables that have potential impact on the electropotential responses is constructed, and analysis of variance tests are carried out to (1) estimate the parameters or coefficients associated with such variables and (2) determine the probability or likelihood that such coefficients are equal to zero. Only those variables having non-zero coefficients at confidence levels of not less than 95% (i.e., the probability of such coefficients being zero is not more than 5%) are selected to be included into a multiple regression model for determination of the organic additive concentrations.

Six (6) non-composition variables have been identified using such analysis of variance tests for analysis of organic additive concentration in copper electroplating solutions, which include (1) nucleation potential (i.e., the potential pulse before current plating); (2) nucleation time, (3) electroplating current, (4) electroplating time, (5) scan rate (i.e., potential change rate) of the cyclic voltammetry during pre-plating cleaning process, and (6) size of the measuring electrode used during the electrochemical analysis.

A multiple regression model including terms for these selected non-compositional variables and for the organic additive concentrations is then established in step (b). An important advantage of the method of the present invention is that it provides terms to account for interactions between the non-compositional variables and/or the additive concentrations.

Once all the coefficients for the non-compositional variables and the additive concentrations in such multiple regression model are determined via calibration, the actual sample analysis starts by conducting three experimental runs, each of which has a different sets of predetermined values for the non-compositional variables. The electroplating potentials of the sample electrochemical deposition solution in such three experimental runs are measured and used to establish three equations according to the established multiple regression model. Each equation contains known coefficients, known values of the non-compositional variables, and the electroplating potential value as measured. The only three unknown values in such equations are the organic additive concentrations, which can be readily determined by solving the three equations.

The three experimental runs can be conducted sequentially in a single electrochemical analytical cell. Alternatively, they can be carried out simultaneously in three electrochemical analytic cells having three different plating protocols or settings.

A further aspect of the present invention relates to a method for simultaneously determining concentrations of suppressor, accelerator, and leveler in a sample electrochemical deposition solution, by using a single electrochemical analytical cell and a single plating protocol, comprising the steps of:

(a) selecting n compositional terms that include suppressor concentration, accelerator concentration, leveler concentration, and interactions between two or more of the additive concentrations, wherein $n \geq 3$;

(b) establishing m multiple regression models that correspond to m time points during the electrochemical metal deposition process, wherein each model expresses electropotential responses of electrochemical deposition solutions as a function of the n selected compositional terms and their corresponding coefficients, wherein $m \geq 3$;

(c) using the electrochemical analytical cell and the plating protocol for measuring electropotential responses of multiple calibration solutions at each of the m time points, wherein such calibration solutions contain suppressor, accelerator, and leveler at unique, known concentrations;

(d) determining the coefficients of the n selected compositional terms for each of the m multiple regression models, based on information obtained in step (c); (e) using the electrochemical analytical cell and the plating protocol for measuring electropotential responses of the sample electrochemical deposition solution at each of the m time points; and (f) determining the n selected compositional terms based on the established multiple regression models, the coefficients determined in step (d), and the electropotential responses measured in step (e); and (g) calculating concentrations of suppressor, accelerator, and leveler in the sample electrochemical deposition solution from the compositional terms so determined.

Matrix inversion can be used for quickly and directly determining the n selected composition terms in step (f). Specifically, three matrixes X, $\beta$, and Y are constructed for representing the m multiple regression models as $Y=\beta X$, wherein X is a n×1 compositional matrix containing the n compositional terms, wherein $\beta$ is a m×n coefficient matrix containing the coefficients determined in step (d), and Y is a m×1 response matrix containing the electropotential responses measured in step (e). The compositional matrix X containing the n compositional terms can be directed determined as $X=(\beta'\beta)^{-1}\beta'Y$, wherein $\beta'$ is the transpose of $\beta$, and wherein $(\beta'\beta)^{-1}$ is the inverse of $\beta'\beta$.

The time points used for establishing the multiple regression models can be selected from any time instances during the electroplating process. For example, they can be selected from 0.2 second, 0.25 second, 0.5 second, 1 second, 5 seconds, 10 seconds, and 20 seconds.

Other aspects, features and embodiments of the invention will be more fully apparent from the ensuing disclosure and appended claims.

DETAILED DESCRIPTION AND PREFERRED EMBODIMENTS THEREOF

The present invention proposes various new electrochemical analytical cell designs and new methodologies for conducting concentration analysis of electrochemical deposition (ECD) solutions, which are described in detail as follows:

Electrochemical Cells with Microelectrodes

In one aspect of the present invention, microelectrodes having cross-sectional diameters of not more than 250 µm are employed for electrochemical analysis of electrochemical deposition solutions, in place of the rotating disc electrodes (RDEs) used in conventional electrochemical cells as described in U.S. Pat. No. 6,280,602 entitled "METHOD AND APPARATUS FOR DETERMINATION OF ADDITIVES IN METAL PLATING BATHS;" U.S. Pat. No. 6,459,011 entitled "APPARATUS FOR DETERMINATION OF ADDITIVES IN METAL PLATING BATHS;" U.S. Pat. No. 6,592,737 entitled "METHOD AND APPARATUS FOR DETERMINATION OF ADDITIVES IN METAL PLATING BATHS;" and U.S. Pat. No. 6,709,568 entitled "METHOD FOR DETERMINING CONCENTRATIONS OF ADDITIVES IN ACID COPPER ELECTROCHEMICAL DEPOSITION BATHS," the contents of which are incorporated by reference herein in their entireties for all purposes.

Specifically, the present invention provides an electrochemical analytical cell comprising a single measurement chamber in which the test electrode, the counter electrode, and the reference electrode are all positioned, wherein at least the test electrode (and optionally the counter and/or reference electrode(s)) is a microelectrode having a cross-sectional diameter within a range of from about 1 µm to about 250 µm, and preferably from about 1 µm to about 125 µm, and more preferably from about 1 µm to about 25 µm. Such microelectrode may comprise any suitable materials, including but not limited to noble metals, noble metal alloy, and vitreous carbon. Preferably, such microelectrode comprises platinum or platinum alloy.

The microelectrode employed by the present invention is sufficiently small to avoid noise disturbance due to liquid fluctuation, thereby significantly enhancing the signal to noise ratio, in comparison with the RDE used in the conventional electrochemical cells. Further, unlike the RDE, the microelectrode does not contain any moving parts and therefore is much more robust and reliable for long-term uses.

Additionally, the single chamber configuration of the electrochemical analytical cell of the present invention allows all three electrodes to be placed adjacent to each other, which is structurally simpler and functionally more reliable, in comparison with the conventional electrochemical cells that comprise a reference chamber for disposing the reference electrode and a separate measuring chamber for disposing the measuring electrode and the counter electrode.

Flow-Through Type Electrochemical Cells

Figure 1:
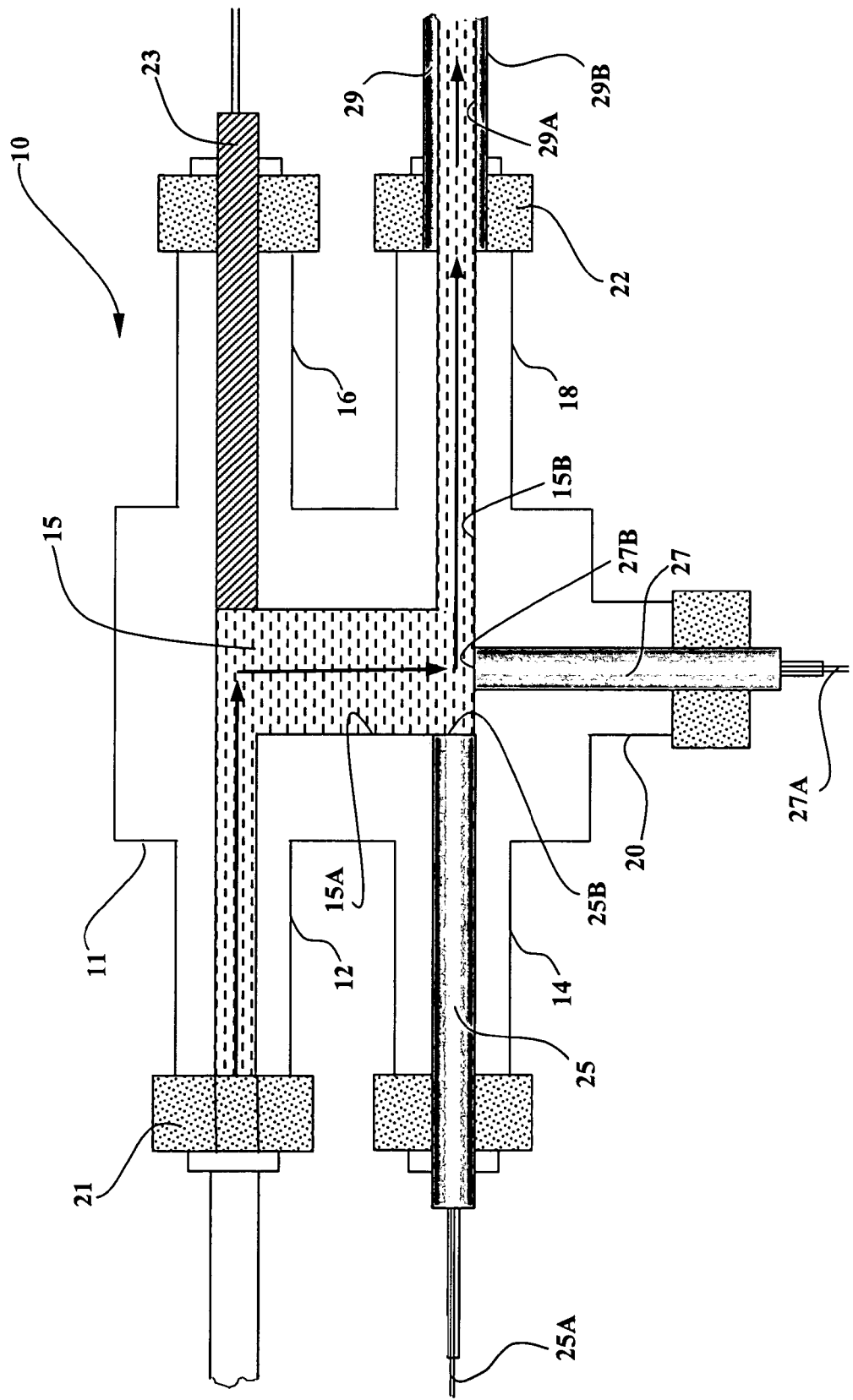
FIG. 1 is a cross-sectional view of an electrochemical analytical cell having a flow-through configuration, according to one embodiment of the present invention.

FIG. 1 shows an electrochemical analytical cell 10 having a flow-through configuration, which is defined as a configuration having a liquid pathway that is free of (or substantially free of) blockage.

Specifically, the electrochemical analytical cell 10 comprises a housing 11 with five leg portions 12, 16, 14, 18, and 20. Such housing 11 defines a single measurement chamber 15, which is in fluid communication with a liquid inlet 21 and an liquid outlet 22.

Such housing further comprises a measuring electrode 25, a reference electrode 27, and a counter electrode 29. Preferably but not necessary, at least the measuring electrode 25, and optionally the reference and counter electrodes 27 and 29, comprises a microelectrode having a cross-sectional diameter of from about 10 µm to about 125 µm. The measurement chamber 15 of the present invention may further comprise one or more temperature sensors 23, for monitoring liquid temperature therein.

The measuring electrode 25 is preferably embedded inside a wall of the measurement chamber 15 around the leg portion 14 and extends through such wall. Electrical connectors 25A of the measuring electrode 25 are placed outside of the measuring chamber 15 for outputting analytical signals obtained during the electrochemical measurement process, while a liquid-contacting surface 25B of such measuring electrode 25 is aligned with an inner surface 15A of the measurement chamber 15, for exposure to the sample electrochemical deposition solution contained therein.

Similarly, the reference electrode 27 is preferably embedded inside a wall of the measurement chamber 15 around the leg portion 18 and extends through such wall. Electrical connectors 27A of the reference electrode 27 are placed outside of the measurement chamber 15 for signal outputting, while a liquid-contacting surface 27B of the reference electrode 27 is aligned with an inner surface 15B of the measurement chamber 15, for exposure to the sample electrochemical deposition solution.

Further, the counter electrode 29 preferably comprises a tubular element having an inner surface 29A and an outer surface 29B. Such counter electrode 29 forms a part of the liquid outlet 22 for flowing of the sample electrochemical deposition (ECD) solution therethrough. In such manner, the inner surface 29A constitutes a liquid-contacting surface that is in direct contact with the sample ECD solution and also in alignment with the inner surface 15B of the measurement chamber 15, while the outer surface 29B can be connected with external electrical connectors (not shown) for application of an electrical potential or current.

The liquid inlet 21, the measurement chamber 15, and the liquid outlet 22 jointly define a liquid path way, which is indicated by the arrowheads in FIG. 1, for passing a sample ECD solution therethrough.

An important advantage of the present invention lies in that all the liquid-contacting surfaces (25B, 27B, 29A) of all the electrodes (25, 27, 29) are aligned with one or more inner surfaces (15A, 15B) of such liquid pathway. In this manner, the liquid pathway is free of blockage by the electrodes, so that a sample ECD solution or a cleaning solution can therefore be used to sweep through the entire cell, for complete removal of chemical residue and minimization of cross-contamination between different sample ECD solutions.

The above-described features of the flow-through type electrochemical cell 10 as illustrated in FIG. 1 can be employed either independently or jointly, or with modifications that are consistent with the spirits and principles of the present invention, for construction of various new electrochemical cells that are within the broad scope of the present invention.

Overflow Type Electrochemical Cells

Figure 2:
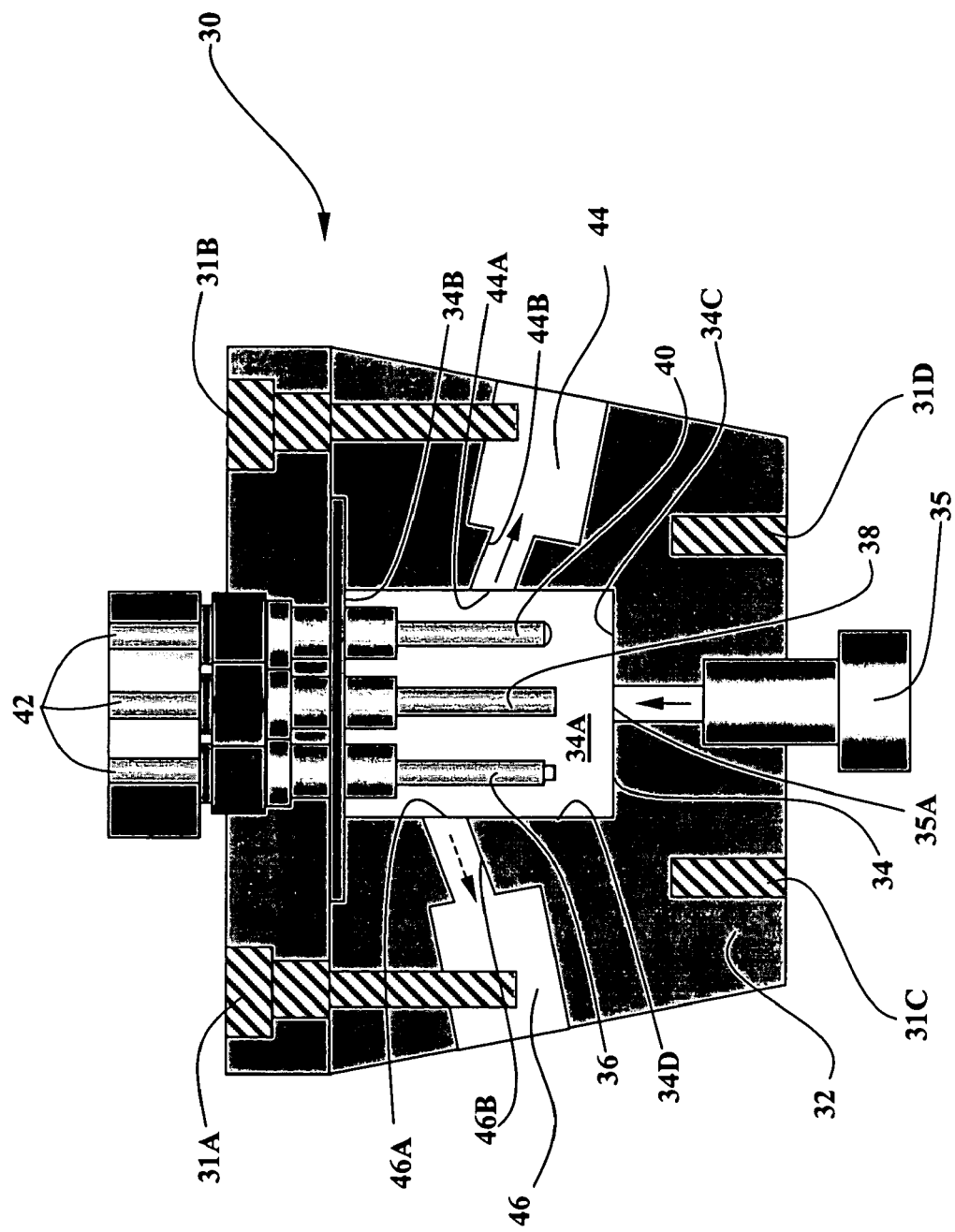
FIG. 2 is a cross-sectional view of an electrochemical analytical cell having an overflow configuration, according to one embodiment of the present invention.

FIG. 2 shows a cross-sectional view of an electrochemical analytical cell 30 having an overflow configuration, which provides a liquid pathway having a direction opposite to the direction of gravity and allows discharge of liquid through overflow.

Specifically, the electrochemical cell 30 comprises a housing 32 mounted by screw members 31A-D. Such housing 32 contains a single measurement chamber 34 having an inner volume 34A defined by a top surface 34B, a bottom surface 34C, and a chamber wall 34D therebetween, and the measurement chamber 34 is in further fluid communication with a liquid inlet 35, a first liquid outlet 44, and a second liquid outlet 46.

A counter electrode 36, a measuring electrode 38, and a reference electrode 40 having external electrical connectors 42 extend from the top surface 34B into the inner volume 34A for contacting the sample ECD solution contained by such measurement chamber 34. Preferably but not necessary, at least the measuring electrode 38, and optionally the reference and counter electrodes 36 and 40, comprises a microelectrode having a cross-sectional diameter of from about 10 µm to about 125 µm.

The liquid inlet 35 comprises an opening 35A on the bottom surface 34C of the measurement chamber 34, while such opening 34A is preferably controlled by a valve for introduction of liquids (e.g., sample ECD solutions and cleaning solutions) from the bottom surface 34C upwardly into the inner volume 34A of the measurement chamber 34.

The first liquid outlet 44 comprises an opening 44A on the chamber wall 34D of the measurement chamber 34, while such opening 44A is preferably controlled by a valve leading to a liquid passage 44B. Such first liquid outlet 44 can be used for discharge of a first liquid (e.g., a sample ECD solution) introduced by the liquid inlet 35. Sine the liquid flow is from bottom up, along a direction that is exactly opposite to the direction of the gravity, discharge of the liquid is effectuated by overflow only, i.e., the liquid enters the outlet opening 44A only when sufficient liquid has been introduced and the liquid level reaches such opening 44A.

Similarly, the second liquid outlet 46 comprises an opening 46A on the chamber wall 34D of the measurement chamber 34, while such opening 46A is preferably controlled by a valve and is in fluid communication with a liquid passage 46B. Such second liquid outlet 46 can be used for discharge of a second liquid (e.g., a cleaning solution) introduced by the liquid inlet 35 by overflow action as described hereinabove.

The difference between the first and second liquid outlets 44 and 46 lies in the fact that the distance between the first outlet opening 44A and the bottom surface 34C of the measurement chamber 34 is shorter than the distance between the second opening 46A and the bottom surface 34C.

In such manner, a sample ECD solution can be introduced into the measuring chamber 34 via liquid inlet 35 before each analysis cycle. Optionally, the measurement chamber 34 can be flushed by a continuous flow of the sample ECD solution (indicated by the solid arrowhead) for a brief period of time, by opening the valves controlling the inlet 35 and the first outlet 44. After the analysis, the valve controlling the first outlet 44 can be opened, for discharge of a portion of the sample ECD solution; subsequently, such first outlet 44 is closed, and the valves controlling the liquid inlet 35 and the second outlet 46 can be opened, for flowing a cleaning solution through the measurement chamber 34 in an overflow manner. Since the first outlet opening 44A is closer to the bottom surface 34C than the second outlet opening 46A, such first outlet opening 44A lies within the flow path of the cleaning solution (indicated by the dotted arrowhead), and overflow of the cleaning solution therefore effectively removes any chemical residue that is left around the first outlet opening 44A by the sample ECD solution last analyzed.

In order to prevent liquid backflow into the inner volume 34A of the measurement chamber 34, the liquid passages 44B and 46B of the first and second liquid outlet 44 and 46 are slanted. Specifically, the ends of such liquid passages 44B and 46B that are adjacent to the respective liquid openings 44A and 46A are higher than the other ends, so that once liquids enter the liquid openings 44A and 46A, they can only flow down the slanted liquid passages 44B and 46B under the force of gravity to outside of the measurement chamber 34, and no liquid accumulation or backflow is possible inside such slanted liquid passages 44B and 46B.

The above-described features of the flow-through type electrochemical cell 30 as illustrated in FIG. 2 can be employed either independently or jointly, or with modifications that are consistent with the spirits and principles of the present invention, for construction of various new electrochemical cells that are within the broad scope of the present invention.

Electrochemical Deposition with an Initial Potential Pulse Followed by Constant Current As described by U.S. Pat. Nos. 6,280,602; 6,459,011; 6,592,737; and 6,709,568, a conventional PCGA measurement cycle that is useful for concentration analysis of ECD solutions typically comprises the following four steps:

(a) stripping, in which the copper layer previously deposited is removed;

(b) cleaning, in which the measuring electrode surface is thoroughly cleaned electrochemically or chemically using an acid bath;

(c) equilibration (optional), in which the measuring electrode and the reference electrode are exposed to the sample ECD solution and allowed reach an equilibrium state; and (d) plating, in which copper is electrochemically deposited onto the measuring electrode under an initial current pulse followed by a constant current, while the plating potential between the measuring and counter electrodes is monitored and recorded.

One problem associated with such conventional PCGA method is that the plating potential signal is not stable during the plating step. As a result, the determinations of organic additive concentrations are not sufficiently accurate for the high-precision control that is desired from the perspective of high-volume manufacturing operations for the next generation of semiconductors, in which reliable metrology is critically important.

The present invention therefore provides a new PCGA method, based on the discovery that use of a potential pulse, in place of a current pulse, followed by constant current plating during the plating step, yields a plating potential signal of significantly enhanced stability and accuracy. Such enhancement of stability and accuracy in turn yields improved measured results for organic additive concentrations in operation of ECD baths.

Specifically, the potential pulse is applied for a sufficient period of time to induce metal nucleation on the electrode surface, and preferably for duration of from about 1 microsecond to about 2.5 seconds. For electrochemical deposition of copper from a sample ECD solution comprising copper sulfate, sulfuric acid, chloride, and one or more organic additives, such potential pulse preferably has a magnitude of from about −0.1V to about −1V, more preferably from about −0.1V to about −0.9V. Magnitude of such potential pulse can be readily modified by a person ordinarily skilled in the art to adapt for electrochemical deposition of other metals or metal alloys using other ECD solutions.

For copper ECD, the constant current following such potential pulse is preferably within a range of from about −1 $mA/cm^2$ to about −1000 $mA/cm^2$, which can be readily modified by a person ordinarily skilled in the art for adaptation to other types of ECD reactions using other ECD solutions.

Figure 3A:
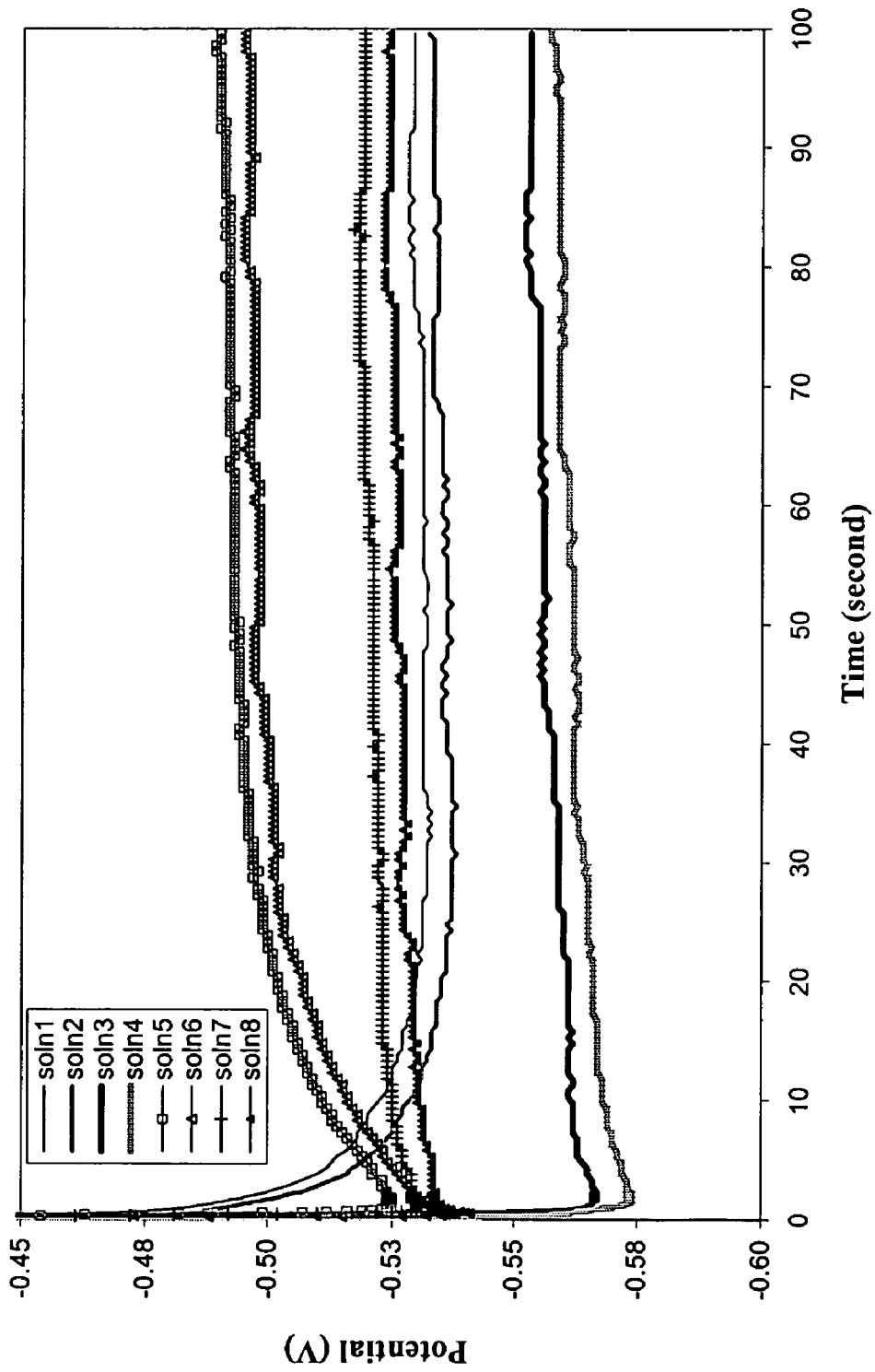
FIG. 3A is a graph of multiple electropotential response curves measured over time for a set of electrochemical deposition solutions containing organic additives at different concentrations, wherein the measurements were conducted with a potential pulse followed by current plating.

FIG. 3A shows the potential response curves of eight (8) different copper ECD solutions containing the suppressor, accelerator, and leveler at different, known concentrations (specified by Table I hereinafter), as measured under a 0.1 second potential pulse of about −0.7V, followed by constant current plating at −100 $mA/cm^2$ for about 100 seconds.

plating, and it constitutes an important advancement in the field of PCGA-based concentration analysis.

Electrochemical Concentration Analysis Using a Five-Step Measurement Cycle

A conventional measurement cycle useful for concentration analysis of copper ECD solutions typically comprises four steps, which include (1) stripping, (2) cleaning, (3) equilibrium, and (4) plating, as described in U.S. Pat. Nos. 6,280,602; 6,459,011; 6,592,737; and 6,709,568.

The present invention provides a new measurement cycle that comprises five steps, including (1) initial stripping, (2) cyclic voltammetry (CV) scan cleaning, (3) equilibrium, (4) plating, and (5) post-plating stripping, for further reducing the risk of cross-contamination between sample ECD solutions that are analyzed by sequentially by the same electrochemical analytical cell and further shortening the run time required for one measurement cycle.

Each steps of such new measurement cycle are described in detail in the ensuring sections:

Electrostripping:

The new measurement cycle of the present invention starts with electrostripping of the measuring electrode, which is carried out by applying a positive potential (i.e., stripping potential) between the measuring electrode and the counter electrode that is sufficient for electrochemically removing the metal residue formed on the measuring electrode during a previous measurement cycle.

When such measurement cycle is used for measuring sample ECD solutions that comprise copper sulfate, sulfuric acid, chloride, and optionally one or more organic additives, the stripping potential is preferably within a range of from about 0.5V to about 1V, and more preferably from about 0.6V to about 0.8V. The duration of the electrostripping is preferably from about 40 seconds to about 200 seconds and more preferably from about 60 seconds to about 120 seconds. Electrostripping at a stripping potential of less than 0.8V and for

TABLE I

| | Additive Concentration (ml/L) | | | | | | | |
| --- | --- | --- | --- | --- | --- | --- | --- | --- |
| | Solution #1 | Solution #2 | Solution #3 | Solution #4 | Solution #5 | Solution #6 | Solution #7 | Solution #8 |
| Accelerator | 3 | 3 | 3 | 3 | 9 | 9 | 9 | 9 |
| Leveler | 1.25 | 1.25 | 3.75 | 3.75 | 1.25 | 1.25 | 3.75 | 3.75 |
| Suppressor | 1 | 3 | 1 | 3 | 1 | 3 | 1 | 3 |

Figure 3B:
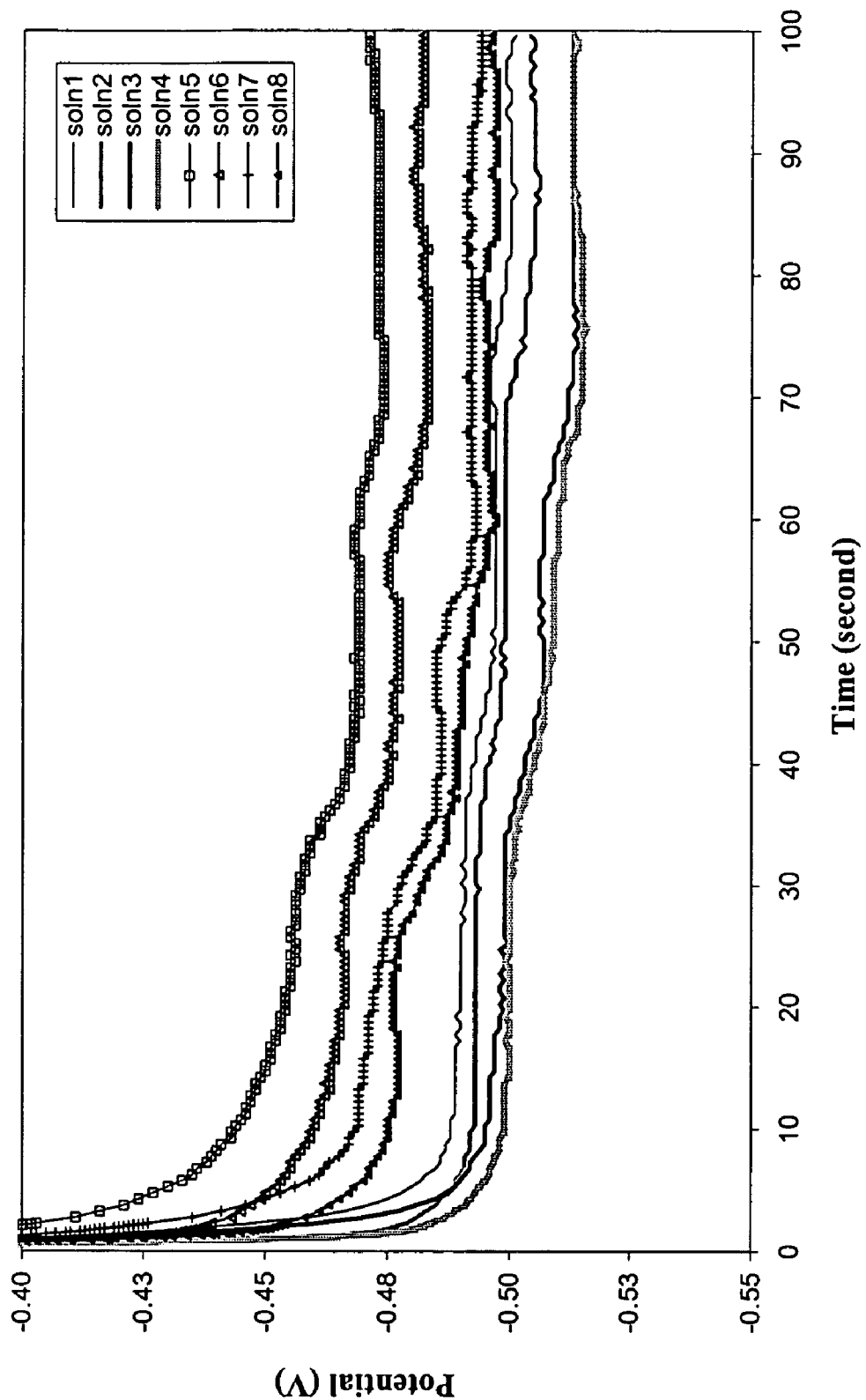
FIG. 3B is a graph of comparative electropotential response curves measured for the same set of electrochemical deposition solutions as in FIG. 3A, wherein the measurements were conducted with a current pulse followed by current plating.

In comparison, FIG. 3B shows the potential response curves of the same solutions #1-8, as measured under a 0.1 second current pulse of about −200 $mA/cm^2$, followed by constant current plating at 100 $mA/cm^2$ for about 100 seconds.

It is evident that the potential response curves in FIG. 3A contain little fluctuations over time and almost no overlapping between the curves, while the potential response curves in FIG. 3B show significant fluctuations over time and overlapping therebetween.

Therefore, use of a potential pulse before constant current plating in the plating process of the present invention provides plating potential signals of significantly enhanced stability and accuracy, in comparison with the conventional plating process that uses a current pulse before the constant current duration of at least twice of the plating duration (i.e., 2×) is particularly suitable for producing reliable and stable measurement results.

An electrolytic cleaning solution containing sulfuric acid is preferably used for conducting the electrostripping of the measuring electrode, by immersing both the measuring and the counter electrodes in such cleaning solution. More preferably, the measurement chamber containing the measuring electrode and counter electrode is flushed with such electrolytic cleaning solution during the electrostripping. The flushing may be carried out through the entire time of the electrostripping, or for only a predetermined period of time (e.g., 10 seconds or 20 seconds). In such manner, at least a portion of the metal residue stripped off the measuring electrode is carried out of the measurement chamber by the electrolytic cleaning solution, thereby reducing the metal concentration in the measurement chamber and reducing the risk of metal re-deposition onto the inner surfaces of the measurement chamber or counter electrode under the stripping potential.

CV Scan Cleaning:

The presence of surface-active organic materials, such as the suppressor, accelerator, and leveler in the sample ECD solution leads to formation of an organic surface residual layer on the surface of the measuring electrode, resulting in electrode passivation or a change in the electrode surface state, and causing significant measurement errors after such measuring electrode is used for an extended period of time. Maintenance of a clean, reproducible electrode surface therefore is of critical importance in making meaningful electroanalytical measurements.

The present invention therefore provides a cyclic voltammetry-based (CV scan) cleaning step for removing the organic surface residue from the measuring electrode. CV scan is particularly effective for in situ cleaning and depassivating the electrode, with significantly shortened system down time and reduced damages to the electrode surface.

Specifically, a cyclic electropotential is applied between the measuring electrode and the counter electrode, while both electrodes are immersed in either a sample ECD solution or an electrolytic cleaning solution as described hereinabove. Effective cleaning can be achieve by a cyclic electropotential that oscillates between about −4V to about +4V, more preferably from about −1V to about +1V, and most preferably from about −0.7V to about 0.25V. Within such cycling range, the cyclic electropotential oxidizes and/or reduces the organic surface residue absorbed on the measuring electrode, therefore depassivating the measuring electrode. Further, such cyclic electropotential also generates multiple hydrogen and oxygen micro-bubbles on the electrode surface within such cyclic range, therefore providing a vigorous surface process that functions to peel away any non-oxidizable or non-reducible solid or liquid residues on the electrode surface.

The scan rate (i.e., potential change rate) of the CV scan is preferably within the range of from about 0.1V/second to about 0.5V/second and more preferably from about 0.2V/second to about 0.4V/second.

The CV scan duration is preferably at least 10 cycles, and more preferably at least 15 cycles, and most preferably at least 20 cycles.

When the measurement cycle is used for measuring sample ECD solutions that comprise copper sulfate, sulfuric acid, chloride, and optionally one or more organic additives, an electrolytic cleaning solution containing sulfuric acid as described hereinabove is preferably used for conducting the CV scan cleaning step. More preferably, the measurement chamber containing the measuring electrode and counter electrode is flushed with such electrolytic cleaning solution during the CV scan cleaning, so as to carry the organic surface residue out of the measurement chamber and reduce cross-contamination thereby.

Equilibrium:

After the stripping and cleaning steps and before the actual plating, the measurement chamber is filled with a fresh sample ECD solution to be analyzed, and the measuring and counter electrodes are both immersed in such fresh sample ECD solution for a sufficient period of time until a steady state or an equilibrium state is reached.

Such equilibrium state can be reached either by disconnecting the measuring electrode from the counter electrode to form an open circuit with no electrical current passing therethrough, or by maintaining a closed circuit while applying between the measuring and counter electrodes a predetermined electropotential that is less than the plating potential required. In a specific embodiment of the present application, a two-stage equilibrium is achieved by applying a potential of from about −1V to about −0.1V during a first stage, and a potential of from about 0.1V to about 1V during a second stage, wherein the duration of the first stage is at least twice longer than the second stage. Preferably, during such first stage of the equilibrium, the sample ECD solution is continuously flushed through the measurement chamber.

Plating:

Metal electroplating in the present invention is preferable carried out at constant plating current, while the potential response of the sample ECD solution is concurrently monitored as an analytical signal for determining the organic additive concentrations in such sample solution.

Constant plating current within a range of from about −1 mA/cm$^2$ to about −1000 mA/cm$^2$, preferably from about −10 mA/cm$^2$ to about −500 mA/cm$^2$, is sufficient for electrochemical metal deposition, and the plating duration is preferably from about 10 seconds to about 60 seconds, more preferably from 10 seconds to about 30 seconds, and most preferably from about 15 seconds to about 25 seconds.

Preferably but not necessarily, the constant current plating is preceded by a potential pulse of from about −0. V to about −1V, which lasts only from about 1 microsecond to about 2.5 seconds. Such potential pulse is particularly useful for optimizing metal nucleation on the electrode surface and stabilizing the potential signals during the subsequent current plating stage.

Post-Plating Stripping:

The metal deposition layer formed on the measuring electrode during the plating step, if not timely removed, may alloy with the metal component of the measuring electrode, thereby deleteriously changing the surface state of the measuring electrode in an irreversible manner and causing significant measurement errors for future measurements.

Since the time interval between two adjacent measurement cycles may vary significantly, it is important to ensure timely removal of such metal deposition layer and avoid formation of alloy between such metal deposition layer and the metal component of the measuring electrode.

The present invention therefore provides post-plating electrostripping immediately after the plating step, to remove at least a portion of the metal deposition layer before the commencement of the next measurement cycle. Therefore, prolonged time intervals between measurement cycles will no longer cause surface state changes of the measuring electrode or reduce the measurement accuracy.

Such post-plating electrostripping can be carried out by applying a positive potential (i.e., the stripping potential) of from about 0.1V to about 0.3V between the measuring electrode and the counter electrode for from about 20 seconds to about 60 seconds.

An electrolytic cleaning solution containing sulfuric acid is preferably used for conducting the post-plating electrostripping. More preferably, the measurement chamber containing the measuring electrode and counter electrode is flushed with such electrolytic cleaning solution, either throughout the post-plating electrostripping step or for at least a sufficient period of time (e.g., 20 to 40 seconds).

Figure 4A:
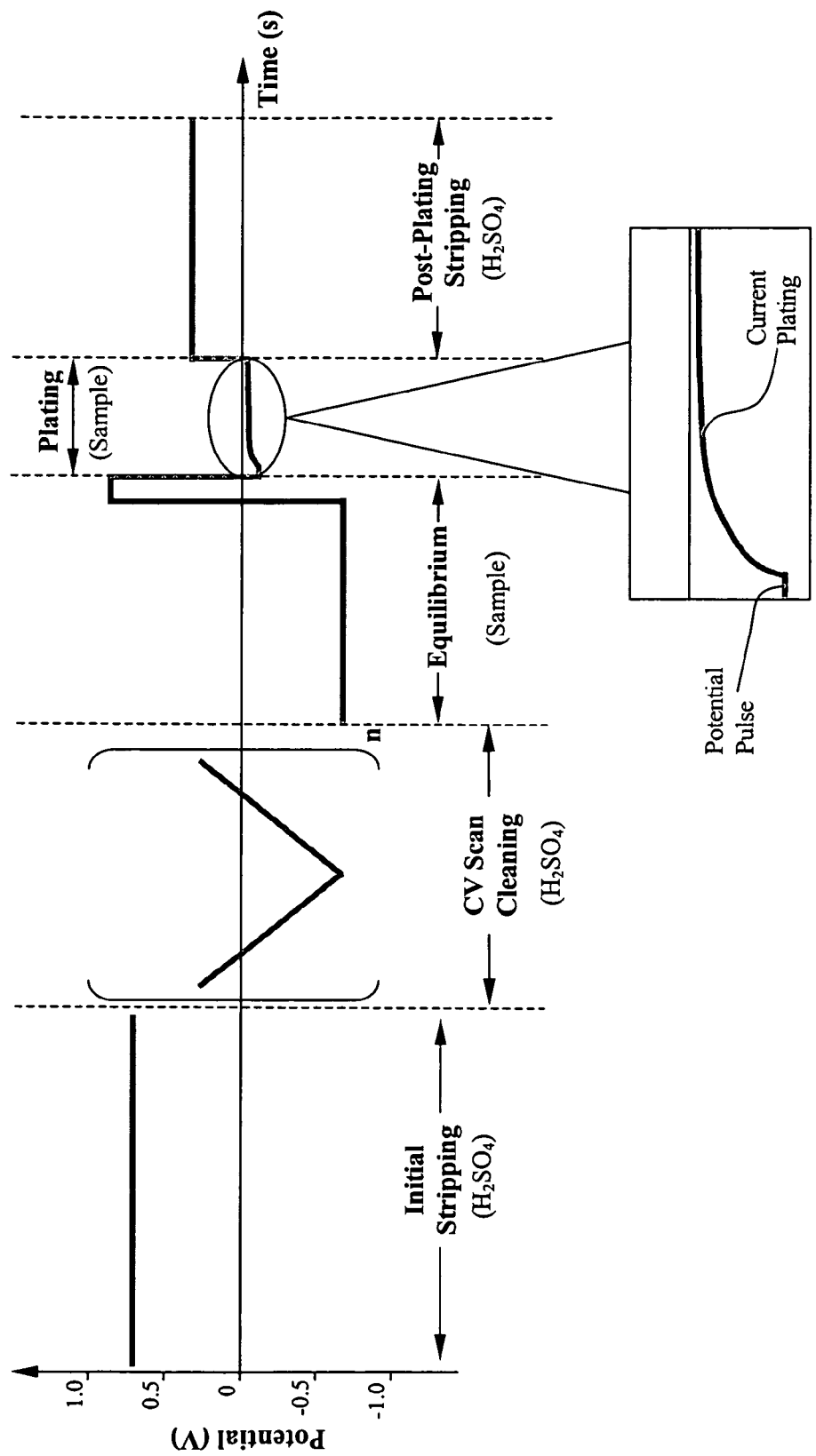
FIGS. 4A and 4B are illustrative potential waveforms during exemplary measurement cycles, according to two alternative embodiments of the present invention.
Figure 4B:
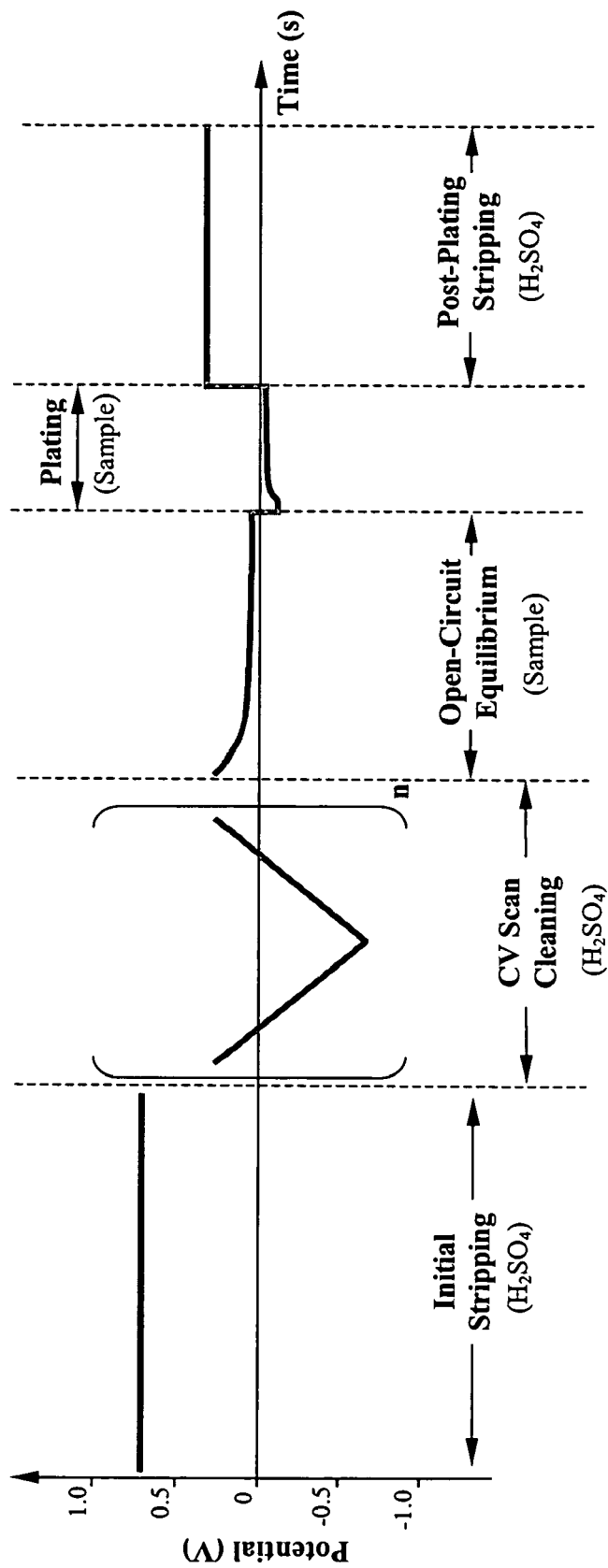

FIGS. 4A and 4B shows the potential waveforms for two measurement cycle, according to two slightly different embodiments of the present invention.

Specifically, FIG. 4A shows a measurement cycle that comprises (1) an initial electrostripping carried out in a sulfuric acid cleaning solution at a stripping potential of about 0.7V for about 80-100 seconds, during which the sulfuric acid cleaning solution flushes the measurement chamber for about 10 seconds; (2) CV scan cleaning carried out in a sulfuric acid cleaning solution at a cyclic potential that oscillates between −0.7V to about 0.25V for about 20 cycles (i.e., n=20) with a scan rate of about 0.3V/second, throughout which the sulfuric acid cleaning solution continuously flushes the measurement chamber; (3) two-stage equilibrium carried out in a fresh sample ECD solution with a close circuit between the measuring and counter electrodes, wherein a first potential of about −0.7V is applied for about 80 seconds with the sample ECD solution continuously flushing through the measurement chamber during a first stage, and a second potential of about 0.82V is applied for about 5 seconds in the sample ECD solution; (4) electroplating carried out in the sample ECD solution, by applying an initial potential pulse of about −0.17V for about 0.141 seconds and a subsequent constant plating current of about −940 mA/cm$^2$ for about 20 seconds, during which the potential responses of the sample ECD solution is continuously monitored; and (5) post-plating electrostripping carried out in a sulfuric acid cleaning solution at a stripping potential of about 0.3V for about 40 seconds, throughout which the sulfuric acid continuously flushes the measurement chamber.

FIG. 4B shows a measurement cycle similar to that illustrated in FIG. 4A, except that the equilibrium is reached in an open circuit without sample flushing.

The entire runtime required for the measurement cycle of the present invention is not more than 20 minutes, and typically around 6-10 minutes, which significantly increases the measurement efficiency and enables true real-time ECD bath analysis. Further, such measurement cycle further reduces the risk of cross-contamination between different sample solutions analyzed by the same electrochemical analytical cell and increases the accuracy of the measurement results.

Concentration Analysis Based on a Single Multiple Regression Model

The present invention provides a method for simultaneously determining the concentrations of multiple organic additives, i.e., suppressor, accelerator, and leveler, in a sample ECD solution, based on a single multiple regression model that defines the electroplating potential of the sample solution as a function of multiple variables that represent both the compositional parameters, such as the additive concentrations, as well as non-compositional parameters associated with the measurement cycle.

First, various non-compositional variables that may have potential impacts on the electroplating potential of the sample ECD solution are tested for their respective significance with respect to the electroplating potential. Specifically, electroplating potentials of one or more sample ECD solutions under varying values of the potential non-compositional variables are measured to establish a sample data set for analysis of variance tests, in which the estimated coefficient (i.e., parameter) of each non-compositional variable and the probability that such coefficient may equal zero are determined. The non-compositional variables having non-zero coefficients at confidence levels above a predetermined threshold (for example, not less than 95%, which means that the probability that the coefficients of such variables are not zero is equal to or more than 95%) are selected.

By testing various non-compositional variables, nucleation potential, nucleation time, electroplating current, electroplating time, with or without CV scan cleaning, scan rate of the CV scan, types of cleaning solution used, size of the measuring electrode used, sample solution de-aeration, and equilibrium time have been found to have impact on the electroplating potential. Particularly, the nucleation potential, the nucleation time, the electroplating current, the electroplating time, the CV scan duration, and the size of the measuring electrode influence have significant impact on the plating potential.

A multiple regression model can therefore be established to express the electropotential responses of ECD solutions as a function of one or more above-described non-compositional variables, the organic additives concentrations, and their corresponding coefficients.

Preferably, one or more terms representing the interactions between the organic additive concentrations and the non-compositional variables are included in such multiple regression model. Quadratic terms and/or cubic terms can also be included.

For illustration purposes while without limiting the broad scope of the present application, an exemplary multiple regression model is established as follows:

$$Y = \beta_0 + \beta_1 \times A + \beta_2 \times B + \beta_3 \times C + \beta_4 \times D + \beta_5 \times E + \beta_6 \times Acc +$$
$$\beta_7 \times Lev + \beta_8 \times Sup + \beta_{10} \times A^2 + \beta_{11} \times AC + \beta_{12} \times AE +$$
$$\beta_{13} \times A \times Acc + \beta_{14} \times B^2 + \beta_{15} \times BD + \beta_{16} \times C^2 + \beta_{17} \times CE +$$
$$\beta_{18} \times C \times Lev + \beta_{19} \times D^2 + \beta_{20} \times E^2 + \beta_{21} \times AE \times Lev + \beta_{22} \times AE \times Sup$$

wherein Y is the electroplating potential measured for a sample ECD solution; A is the nucleation potential (V); B is the nucleation time (second); C is the electroplating current (mA/cm$^2$); D is the CV scan duration (second); E is the size of the measuring electrode (µm); Acc is the concentration of the accelerator in the ECD solution; Lev is the concentration of the leveler; Sup is the concentration of the suppressor; AC, AE, BD, and CE represent two-way interactions between the non-compositional variables ABCDE; A×Acc and C×Lev represent two-way interactions between a non-compositional variable and an additive concentration; AE×Lev and AE×Sup represent three way interactions between two non-compositional variables and an additive concentration; $A^2, B^2, C^2, D^2$, and $E^2$ are the quadratic terms of the non-compositional variables ABCDE; $\beta_0$ is the intercept; and $\beta_1$-$\beta_{22}$ are the coefficients for all the terms of the multiple regression model.

The intercept $\beta_0$ and the coefficients $\beta_1$-$\beta_{22}$ of the above multiple regression model can be readily determined by running multiple calibration measurements, each of which measures the electroplating potential of a calibration solution containing the suppressor, the accelerator, and the leveler at known concentrations at predetermined measurement settings, i.e., with predetermined values of the non-compositional variables A, B, C, D, and E.

Subsequently, three experimental runs are designed for measuring the sample ECD solution containing the organic additives at unknown concentrations. Each experimental run is characterized by a unique, predetermined measurement setting, i.e., with predetermined values of the non-compositional variables A, B, C, D, and E.

The electroplating potentials of the sample ECD solution are then measured for these three experimental runs, to establish three equations (I)-(III), as follows:

$$Y_1 = \beta_0 + \beta_1 \times A_1 + \beta_2 \times B_1 + \beta_3 \times C_1 + \beta_4 \times D_1 + \quad (I)$$
$$\beta_5 \times E_1 + \beta_6 \times Acc + \beta_7 \times Lev + \beta_8 \times Sup + \beta_{10} \times A_1^2 +$$
$$\beta_{11} \times A_1 C_1 + \beta_{12} \times A_1 E_1 + \beta_{13} \times A_1 \times Acc + \beta_{14} \times B_1^2 +$$
$$\beta_{15} \times B_1 D_1 + \beta_{16} \times C_1^2 + \beta_{17} \times C_1 E_1 + \beta_{18} \times C_1 \times Lev +$$
$$\beta_{19} \times D_1^2 + \beta_{20} \times E_1^2 + \beta_{21} \times A_1 E_1 \times Lev + \beta_{22} \times A_1 E_1 \times Sup$$

$$Y_2 = \beta_0 + \beta_1 \times A_2 + \beta_2 \times B_2 + \beta_3 \times C_2 + \beta_4 \times D_2 + \quad (II)$$
$$\beta_5 \times E_2 + \beta_6 \times Acc + \beta_7 \times Lev + \beta_8 \times Sup + \beta_{10} \times A_2^2 +$$
$$\beta_{11} \times A_2 C_2 + \beta_{12} \times A_2 E_2 + \beta_{13} \times A_2 \times Acc + \beta_{14} \times B_2^2 +$$
$$\beta_{15} \times B_2 D_2 + \beta_{16} \times C_2^2 + \beta_{17} \times C_2 E_2 + \beta_{18} \times C_2 \times Lev +$$
$$\beta_{19} \times D_2^2 + \beta_{20} \times E_2^2 + \beta_{21} \times A_2 E_2 \times Lev + \beta_{22} \times A_2 E_2 \times Sup$$

$$Y_3 = \beta_0 + \beta_1 \times A_3 + \beta_2 \times B_3 + \beta_3 \times C_3 + \beta_4 \times D_3 + \quad (III)$$
$$\beta_5 \times E_3 + \beta_6 \times Acc + \beta_7 \times Lev + \beta_8 \times Sup + \beta_{10} \times A_3^2 +$$
$$\beta_{11} \times A_3 C_3 + \beta_{12} \times A_3 E_3 + \beta_{13} \times A_3 \times Acc + \beta_{14} \times B_3^2 +$$
$$\beta_{15} \times B_3 D_3 + \beta_{16} \times C_3^2 + \beta_{17} \times C_3 E_3 + \beta_{18} \times C_3 \times Lev +$$
$$\beta_{19} \times D_3^2 + \beta_{20} \times E_3^2 + \beta_{21} \times A_3 E_3 \times Lev + \beta_{22} \times A_3 E_3 \times Sup$$

wherein $Y_1$-$Y_3$ are the electroplating potentials of the sample ECD solution as measured during the three experimental runs, wherein $A_1$-$E_1$, $A_2$-$E_2$, and $A_3$-$E_3$ are the respective predetermined values of the non-compositional variables ABCDE during the three experimental runs.

Therefore, the above-listed three equations contain only three unknown values, i.e., the accelerator concentration (Acc), the leveler concentration (Lev), and the suppressor concentration (Sup). Such unknown concentration values can thus be readily determined by solving the three equations (I)-(III).

The three experimental runs can be carried out sequentially in the same electrochemical analytical cell. Alternatively, they can be carried out simultaneously in three electrochemical analytical cells, each of which operates according to a unique, predetermined measurement protocol with predetermined values for the non-compositional variables ABCDE.

The number and type of non-compositional variables to be included into the multiple regression model can be readily modified by a person ordinarily skilled in the art. The essence of this invention is to use three experimental runs to provide three equations with only three unknown values corresponding to the additive concentrations, which are readily solvable for concentration determination. Therefore, as few as one non-compositional variable and as many as infinite number of variables can be included into the model. When more variables are included, the model is more sophisticated and provides more accurate analytical results.

Concentration Analysis Using a Single Experimental Run

The present invention provide another method for simultaneously determining concentrations of all three organic additive (i.e., accelerator, leveler, and suppressor) in a sample ECD solution within a single experimental run, wherein time is used as a variable for constructing three or more multiple regression models, and wherein interactions between the organic additives are accounted for.

This method, unlike the method described in the previous section, does not rely on usage of any non-compositional variables associated with the experimental settings. Instead, it considers only compositional terms associated with the additive concentrations and the interactions therebetween.

The concentrations of accelerator, leveler, and suppressor are the three basic and necessary compositional variables to be included. Additional compositional terms representing interactions between the additives or quadratic/cubic terms may also be included. For example, additional compositional terms have potential impacts on the electroplating potential of the sample ECD solution can be tested for their respective significance with respect to the electroplating potential. Specifically, electroplating potentials of one or more sample ECD solutions under varying values of such additional compositional terms are measured to establish a sample data set for analysis of variance tests, in which the estimated coefficient (i.e., parameter) of each additional compositional term and the probability that such coefficient may equal zero are determined. The additional compositional terms having non-zero coefficients at confidence levels above a predetermined threshold (for example, not less than 95%, which means that the probability that the coefficients of such variables are not zero is equal to or more than 95%) can be selected for inclusion.

For illustrative purposes, the following nine (9) compositional terms can be selected, which include:

| | |
|---|---|
| A | Accelerator concentration |
| B | Leveler concentration |
| C | Suppressor concentration |
| AB | Interaction between accelerator and leveler |
| AC | Interaction between accelerator and suppressor |
| ABC | Interaction between accelerator, leveler, and suppressor |
| AA | Quadratic term for accelerator |
| BB | Quadratic term for leveler |
| CC | Quadratic term for suppressor |

The selected compositional terms can then be used to establish m multiple regression models that corresponds to m time points ($t_1, t_2, \ldots t_m$) during the electrochemical metal deposition process, wherein each model expresses electropotential responses of the ECD solutions as a function of the selected compositional terms and their corresponding coefficients, wherein $m \geq 3$.

For example, three multiple regression models that correspond to three time points ($t_1, t_2,$ and $t_3$) can be established, as follows:

$$Y_1 = \beta_A^1 \times A + \beta_B^1 \times B + \beta_C^1 \times C + \beta_{AB}^1 \times AB + \beta_{AC}^1 \times AC +$$
$$\beta_{ABC}^1 \times ABC + \beta_{AA}^1 \times AA + \beta_{BB}^1 \times BB + \beta_{CC}^1 \times CC$$

$$Y_2 = \beta_A^2 \times A + \beta_B^2 \times B + \beta_C^2 \times C + \beta_{AB}^2 \times AB + \beta_{AC}^2 \times AC +$$
$$\beta_{ABC}^2 \times ABC + \beta_{AA}^2 \times AA + \beta_{BB}^2 \times BB + \beta_{CC}^2 \times CC$$

$$Y_3 = \beta_A^3 \times A + \beta_B^3 \times B + \beta_C^3 \times C + \beta_{AB}^3 \times AB + \beta_{AC}^3 \times AC +$$
$$\beta_{ABC}^3 \times ABC + \beta_{AA}^3 \times AA + \beta_{BB}^3 \times BB + \beta_{CC}^3 \times CC$$

wherein $Y_1$, $Y_2$, and $Y_3$ are the electroplating potentials measured at respective time points $t_1$, $t_2$, and $t_3$; $\beta_A^1$-$\beta_{CC}^1$ are the coefficients for the selected compositional terms A-CC at time point $t_1$; $\beta_A^2$-$\beta_{CC}^2$ are the coefficients for the selected compositional terms A-CC at time point $t_2$; $\beta_A^3$-$\beta_{CC}^3$ are the coefficients for the selected compositional terms A-CC at time point $t_3$.

The values of the coefficients $\beta_A^1$-$\beta_{CC}^1$, $\beta_A^2$-$\beta_{CC}^2$, and $\beta_A^3$-$\beta CC^3$ can be readily determined by running multiple calibration measurements of various calibration solutions having unique, known organic additive concentrations, and during each calibration measurement, the electroplating potential is measured three times, at each of the time points $t_1$, $t_2$, and $t_3$.

Subsequently, a single experimental run is carried out for measurement of the sample ECD solution that contains the accelerator, leveler, and suppressor at unknown concentrations. Electroplating potentials of such sample ECD solution at the three time points $t_1$, $t_2$, and $t_3$ are sequentially measured during the experimental run and recorded as $Y_1$, $Y_2$, and $Y_3$.

Based on the three multiple regression models established hereinabove, the coefficient values determined via calibration measurements, and the electroplating potentials measured during the experimental run, one can readily calculating the organic additive concentrations A, B, and C.

A quick and direct method for calculating the organic additive concentrations relies on matrix inversion. Specifically, three matrices X, β, and Y are constructed as follows:

$$X = \begin{pmatrix} A \\ B \\ C \\ AB \\ AC \\ ABC \\ AA \\ BB \\ CC \end{pmatrix}$$

$$\beta = \begin{pmatrix} \beta_A^1 & \beta_B^1 & \beta_C^1 & \beta_{AB}^1 & \beta_{AC}^1 & \beta_{ABC}^1 & \beta_{AA}^1 & \beta_{BB}^1 & \beta_{CC}^1 \\ \beta_A^2 & \beta_B^2 & \beta_C^2 & \beta_{AB}^2 & \beta_{AC}^2 & \beta_{ABC}^2 & \beta_{AA}^2 & \beta_{BB}^2 & \beta_{CC}^2 \\ \beta_A^3 & \beta_B^3 & \beta_C^3 & \beta_{AB}^3 & \beta_{AC}^3 & \beta_{ABC}^3 & \beta_{AA}^3 & \beta_{BB}^3 & \beta_{CC}^3 \end{pmatrix}$$

$$Y = \begin{pmatrix} Y_1 \\ Y_2 \\ Y_3 \end{pmatrix}$$

The three multiple regression models as described herein above can be represented by a simple matrix-based model that defines Y=βX, wherein X is a compositional matrix containing the selected compositional terms, wherein β is a coefficient matrix containing the coefficients determined via calibration measurements, and Y is a response matrix containing the electropotential responses measured via experimental run.

Since both matrices β and Y contain known elements (i.e., $\beta_A^1$-$\beta_{CC}^1$, $\beta_A^2$-$\beta_{CC}^2$, $\beta_A^3$-$\beta_{CC}^3$, and $Y_1$-$Y_2$), they can be used to determined the unknown elements (i.e., A, B, C, ... CC) contained in matrix X.

From βX=Y, the following can be obtained:

$(\beta'\beta)X = Y\beta'$ $(\beta'\beta)^{-1}(\beta'\beta)X = Y\beta'(\beta'\beta)^{-1}$ wherein β' is the transpose of β, and wherein $(\beta'\beta)^{-1}$ is the inverse of β' β.

Since $(\beta'\beta)^{-1}(\beta'\beta)$ equals the identity matrix I, and since the product of identity matrix I with any matrix A will still be A, we can derive X as:

$X = Y\beta'(\beta'\beta)^{-1}$

When β is known, its transpose β' and the inverse of their product $(\beta'\beta)^{-1}$ can be readily calculated. Therefore, the concentrations of the accelerator, leveler, and suppressor (A, B, and C) can be directly determined as the elements of the matrix X.

The above example uses nine compositional terms and three multiple regression models for simplicity. In practice, the number of compositional terms can be more or less than nine (but not less than three), while more than three multiple regression models can be used.

In general, n compositional terms can be selected to establish m multiple regression models (n≧3, and m≧3), as follows:

$Y_1 = \beta_{11} \times X_1 + \beta_{12} \times X_2 + \beta_{13} \times X_3 + \ldots + \beta_{1n} \times X_n$ $Y_2 = \beta_{21} \times X_1 + \beta_{22} \times X_2 + \beta_{23} \times X_3 + \ldots + \beta_{2n} \times X_n$ $Y_3 = \beta_{31} \times X_1 + \beta_{32} \times X_2 + \beta_{33} \times X_3 + \ldots + \beta_{3n} \times X_n$ $\ldots$ $Y_m = \beta_{m1} \times X_1 + \beta_{m2} \times X_2 + \beta_{m3} \times X_3 + \ldots + \beta_{mn} \times X_n$ wherein $X_1$, $X_2$, $X_3$, ..., $X_n$ are the n selected compositional terms; $Y_1$, $Y_2$, $Y_3$, ..., $Y_m$ are the electroplating potentials measured at m time points $t_1$, $t_2$, $t_3$, ..., $t_m$; $\beta_{11}$-$\beta_{1n}$ are the coefficients for the selected compositional terms $X_1$-$X_n$ at time point $t_1$; $\beta_{21}$-$\beta_{2n}$ are the coefficients for the selected compositional terms $X_1$-$X_n$ at time point $t_2$; $\beta_{31}$-$\beta_{3n}$ are the coefficients for the selected compositional terms $X_1$-$X_n$ at time point $t_3$; ...; and $\beta_{m1}$-$\beta_{mn}$ are the coefficients for the selected compositional terms $X_1$-$X_n$ at time point $t_m$.

The three matrices X, β, and Y can then be constructed as follows:

$$X = \begin{pmatrix} X_1 \\ X_2 \\ X_3 \\ \ldots \\ X_n \end{pmatrix}$$

$$\beta = \begin{pmatrix} \beta_{11} & \beta_{12} & \beta_{13} & \ldots & \beta_{1n} \\ \beta_{21} & \beta_{22} & \beta_{23} & \ldots & \beta_{2n} \\ \beta_{31} & \beta_{32} & \beta_{33} & \ldots & \beta_{3n} \\ \ldots & \ldots & \ldots & \ldots & \ldots \\ \beta_{m1} & \beta_{m2} & \beta_{m3} & \ldots & \beta_{mn} \end{pmatrix}$$

$$Y = \begin{pmatrix} Y_1 \\ Y_2 \\ Y_3 \\ \ldots \\ Y_m \end{pmatrix}$$

As shown, the generalized compositional matrix X is a n×1 matrix containing the n compositional terms; the generalized coefficient matrix β is a m×n matrix; and the generalized response matrix Y is a m×1 matrix.

Various time points during the electrochemical deposition process can be selected for constructing the multiple regression models. For example, for constructing the three multiple regression models as illustrated hereinabove, the time points at 5 seconds, 10 seconds, and 20 seconds can be used, while additional time points at 0.2 second, 0.25 second, 0.5 second, and 1 second can also be used.

While the ensuing description of the invention contains reference to illustrative embodiments and features, it will be recognized that the methodology and apparatus of the invention are not thus limited, but rather generally extend to and encompass the determination of analytes in fluid media. For example, although the present description is directed primarily to copper ECD deposition analysis, the invention is readily applicable to other ECD processes, including deposition of silver, gold, iridium, palladium, tantalum, titanium, chromium, cobalt, tungsten, etc., as well as deposition of alloys and deposition of amalgams such as solder.

Examples of additional applications of the invention other than ECD plating of semiconductor device structures include analysis of reagents in reaction media for production of therapeutic agents such as pharmaceutical products, and biotechnology applications involving the concentrations of specific analytes in human blood or plasma. It will therefore be appreciated that the invention is of broad application, and that the ECD system and method described hereafter is but one of a myriad of potential uses for which the invention may be employed.

What is claimed is:

1. An electrochemical cell for analyzing a sample electrochemical deposition solution, comprising (1) a single measurement chamber for receiving the sample electrochemical deposition solution, said measurement chamber being in fluid communication with at least one liquid inlet and at least one liquid outlet, (2) a test electrode, a counter electrode, and a reference electrode positioned in said measurement chamber for contacting the sample electrochemical deposition solution, wherein said test electrode has a longitudinal axis and is characterized by an average transverse dimension of from about 1 µm to about 250 µm, as measured along a direction that is perpendicular to said longitudinal axis, wherein said test electrode does not extend into said measurement chamber, but terminates at a flat end surface that is flush with an inner surface of the measurement chamber so that the test electrode contacts said solution when present in said measurement chamber only at said flat end surface of the test electrode, wherein the counter electrode comprises a tubular element having an inner surface and an outer surface and whose hollow center serves as a liquid pathway for the electrochemical deposition solution, wherein the tubular counter electrode forms a part of the liquid outlet and serves as the liquid pathway for the sample electrochemical deposition solution to pass therethrough, wherein said inner surface of the counter electrode constitutes the only liquid contacting surface of said counter electrode, and wherein said counter electrode maintains contact with sample electrochemical deposition solution at its inner surface and connects to external electrical connectors at its outer surface.

2. The electrochemical cell of claim 1, wherein said test electrode has a cross-sectional diameter within a range of from about 1 µm to about 125 µm.

3. The electrochemical cell of claim 1, wherein said test electrode comprises platinum or platinum alloy.

4. The electrochemical cell of claim 1, wherein the liquid inlet, the liquid outlet, and said measurement chamber define a liquid pathway therethrough, wherein each of the test electrode, the counter electrode, and the reference electrode comprises one or more liquid-contacting surfaces, and wherein the test electrode, the counter electrode, and the reference electrode are arranged and constructed so that all of the liquid-contacting surfaces of said electrodes are flush with one or more inner surfaces of the liquid inlet, the liquid outlet, and/or the measurement chamber, such that the liquid pathway is free of blockage by the electrodes.

5. The electrochemical cell of claim 1, wherein said test electrode is embedded in a wall of said measurement chamber, and comprises electrical connectors extending outside of said measurement chamber.

6. The electrochemical cell of claim 1, wherein said reference electrode is embedded in a wall of said measurement chamber, said reference electrode comprising (1) electrical connectors extending outside of said measurement chamber, and (2) terminating at a flat end surface constituting a liquid-contacting surface that is flush with an inner surface of the measurement chamber for contacting sample electrochemical deposition solution therein, wherein said flat end surface of the reference electrode flush with the inner surface of the measurement chamber constitutes the only liquid-contacting surface of said reference electrode, such that the liquid pathway is free of blockage by the reference electrode.

7. The electrochemical cell of claim 1, wherein said measurement chamber further comprises one or more temperature sensors for monitoring liquid temperature therewithin.

8. The electrochemical cell of claim 1, wherein the measurement chamber comprises five leg portions, with the test electrode embedded in a first leg, the reference electrode embedded in a second leg, and the counter electrode is coupled with a third leg.

9. The electrochemical cell of claim 8, further comprising a temperature sensor in a fourth leg, and a liquid inlet coupled with a fifth leg.

10. An electrochemical cell for analyzing a sample electrochemical deposition solution, including a measurement chamber comprising an inner volume defined by a bottom surface, a top surface and a chamber wall therebetween, with a liquid inlet and a liquid outlet communicating with the inner volume of the measurement chamber, and a test electrode, a counter electrode and a reference electrode in the measurement chamber, wherein the test electrode, the counter electrode, and the reference electrode extend from the top surface downwardly into the inner volume of said measurement chamber in parallel side by side relationship to one another, each terminating at a lower end and having a substantially similar length measured from the top surface of the measurement chamber to its lower end, and wherein the liquid inlet comprises an opening on the bottom surface of said measurement chamber for introducing liquid from the bottom surface upwardly into the inner volume of the measurement chamber, wherein said measurement chamber comprises a first and a second liquid outlet, wherein said first liquid outlet comprises a first opening on the chamber wall, wherein said second liquid outlet comprises a second opening on the chamber wall positioned such that the distance between the first opening and the bottom surface is greater than the distance between the ends of the electrodes extending downwardly into the inner volume of the chamber and the bottom surface, and wherein the distance between said first opening and the bottom surface of the measurement chamber is less than the distance between said second opening and the bottom surface of the measurement chamber.

11. The electrochemical cell of claim 10, wherein the liquid outlet comprises an opening on the chamber wall wherein the distance between the opening on the chamber wall and the bottom surface of the chamber is greater than the distance between the ends of the electrodes extending downwardly into the inner volume of the chamber and the bottom surface.

12. The electrochemical cell of claim 11, wherein the liquid outlet further comprises a liquid passage in fluid communication with the opening, and said liquid passage is slanted in a downward direction so as to prevent liquid backflow into the inner volume of the measurement chamber.

13. An electrochemical cell for analyzing a sample electrochemical deposition solution, including a measurement chamber comprising an inner volume defined by a bottom surface, a top surface and a chamber wall therebetween, with a liquid inlet and a liquid outlet communicating with the inner volume of the measurement chamber, and a test electrode, a counter electrode and a reference electrode in the measurement chamber, wherein the test electrode, the counter electrode, and the reference electrode extend from the top surface downwardly into the inner volume of said measurement chamber in parallel side by side relationship to one another, each terminating at a lower end and having a substantially similar length measured from the top surface of the measurement chamber to its lower end, and wherein the liquid inlet comprises an opening on the bottom surface of said measurement chamber for introducing liquid from the bottom surface upwardly into the inner volume of the measurement chamber, wherein said measurement chamber comprises a first and a second liquid outlet, wherein said first liquid outlet comprises a first opening on the chamber wall, wherein said second liquid outlet comprises a second opening on the chamber wall positioned such that the distance between the first opening and the bottom surface is greater than the distance between the ends of the electrodes extending downwardly into the inner volume of the chamber and the bottom surface, and wherein the distance between said first opening and the bottom surface of the measurement chamber is less than the distance between said second opening and the bottom surface of the measurement chamber, wherein at least one of the first and the second liquid outlet comprises a liquid passage in fluid communication with the respective opening, wherein said liquid passage is slanted in a downward direction so as to prevent liquid backflow into the inner volume of the measurement chamber.

* * * * *

UNITED STATES PATENT AND TRADEMARK OFFICE
CERTIFICATE OF CORRECTION

PATENT NO. : 7,435,320 B2
APPLICATION NO. : 10/836546
DATED : October 14, 2008
INVENTOR(S) : Jianwen Han It is certified that error appears in the above-identified patent and that said Letters Patent is hereby corrected as shown below:

Column 6, line 43, a carriage return should be inserted between "(c);" and "(e)".

Column 14, line 24, "-0. V" should be -- -0.1V --.

Column 18, lines 44-51:

"
$$Y_1 = \beta_A^1 \times A + \beta_B^1 \times B + \beta_C^1 \times C + \beta_{AB}^1 \times AB + \beta_{AC}^1 \times AC + \beta_{ABC}^1 \times ABC + \beta_{AA}^1 \times AA + \beta_{BB}^1 \times BB + \beta_{CC}^1 \times CC$$
$$Y_2 = \beta_A^2 \times A + \beta_B^2 \times B + \beta_C^2 \times C + \beta_{AB}^2 \times AB + \beta_{AC}^2 \times AC + \beta_{ABC}^2 \times ABC + \beta_{AA}^2 \times AA + \beta_{BB}^2 \times BB + \beta_{CC}^2 \times CC$$
$$Y_3 = \beta_A^3 \times A + \beta_B^3 \times B + \beta_C^3 \times C + \beta_{AB}^3 \times AB + \beta_{AC}^3 \times AC + \beta_{ABC}^3 \times ABC + \beta_{AA}^3 \times AA + \beta_{BB}^3 \times BB + \beta_{CC}^3 \times CC$$
"

should be

--
$$Y_1 = \beta_A{}^1 \times A + \beta_B{}^1 \times B + \beta_C{}^1 \times C + \beta_{AB}{}^1 \times AB + \beta_{AC}{}^1 \times AC + \beta_{ABC}{}^1 \times ABC + \beta_{AA}{}^1 \times AA + \beta_{BB}{}^1 \times BB + \beta_{CC}{}^1 \times CC$$
$$Y_2 = \beta_A{}^2 \times A + \beta_B{}^2 \times B + \beta_C{}^2 \times C + \beta_{AB}{}^2 \times AB + \beta_{AC}{}^2 \times AC + \beta_{ABC}{}^2 \times ABC + \beta_{AA}{}^2 \times AA + \beta_{BB}{}^2 \times BB + \beta_{CC}{}^2 \times CC$$
$$Y_3 = \beta_A{}^3 \times A + \beta_B{}^3 \times B + \beta_C{}^3 \times C + \beta_{AB}{}^3 \times AB + \beta_{AC}{}^3 \times AC + \beta_{ABC}{}^3 \times ABC + \beta_{AA}{}^3 \times AA + \beta_{BB}{}^3 \times BB + \beta_{CC}{}^3 \times CC$$
--.

Column 18, line 62, "βCC³" should be -- βcc³ --.

UNITED STATES PATENT AND TRADEMARK OFFICE
CERTIFICATE OF CORRECTION

PATENT NO. : 7,435,320 B2
APPLICATION NO. : 10/836546
DATED : October 14, 2008
INVENTOR(S) : Jianwen Han It is certified that error appears in the above-identified patent and that said Letters Patent is hereby corrected as shown below:

Column 19, lines 29, 31:

"
$$\beta = \begin{pmatrix} \beta^1_A & \beta^1_B & \beta^1_C & \beta^1_{AB} & \beta^1_{AC} & \beta^1_{ABC} & \beta^1_{AA} & \beta^1_{BB} & \beta^1_{CC} \\ \beta^2_A & \beta^2_B & \beta^2_C & \beta^2_{AB} & \beta^2_{AC} & \beta^2_{ABC} & \beta^2_{AA} & \beta^2_{BB} & \beta^2_{CC} \\ \beta^3_A & \beta^3_B & \beta^3_C & \beta^3_{AB} & \beta^3_{AC} & \beta^3_{ABC} & \beta^3_{AA} & \beta^3_{BB} & \beta^3_{CC} \end{pmatrix}$$
"

should be

--
$$\beta = \begin{pmatrix} \beta_A{}^1 & \beta_B{}^1 & \beta_C{}^1 & \beta_{AB}{}^1 & \beta_{AC}{}^1 & \beta_{ABC}{}^1 & \beta_{AA}{}^1 & \beta_{BB}{}^1 & \beta_{CC}{}^1 \\ \beta_A{}^2 & \beta_B{}^2 & \beta_C{}^2 & \beta_{AB}{}^2 & \beta_{AC}{}^2 & \beta_{ABC}{}^2 & \beta_{AA}{}^2 & \beta_{BB}{}^2 & \beta_{CC}{}^2 \\ \beta_A{}^3 & \beta_B{}^3 & \beta_C{}^3 & \beta_{AB}{}^3 & \beta_{AC}{}^3 & \beta_{ABC}{}^3 & \beta_{AA}{}^3 & \beta_{BB}{}^3 & \beta_{CC}{}^3 \end{pmatrix}$$
--.

Signed and Sealed this

Tenth Day of February, 2009

*John Doll*

JOHN DOLL
*Acting Director of the United States Patent and Trademark Office*